(12) United States Patent
Grisenti et al.

(10) Patent No.: US 10,961,257 B2
(45) Date of Patent: *Mar. 30, 2021

(54) POLYMORPHIC MIXTURE OF RIFAXIMIN AND ITS USE FOR THE PREPARATION OF SOLID FORMULATIONS

(71) Applicant: AMRI Italy S.r.L., Milan (IT)

(72) Inventors: Paride Grisenti, Milan (IT); Maria Argese, Sedriano (IT); Daniele Pengo, Paderno Dungnana (IT); Maria Donata Grilli, Cusano Milanino (IT); Emanuela Fumagalli, Lainate (IT); Giuseppe Motta, Rescaldina (IT)

(73) Assignee: AMRI ITALY S.R.L., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/569,275

(22) Filed: Sep. 12, 2019

(65) Prior Publication Data

US 2020/0002357 A1    Jan. 2, 2020

Related U.S. Application Data

(63) Continuation of application No. 15/300,879, filed as application No. PCT/EP2015/056304 on Mar. 24, 2015, now Pat. No. 10,556,915.

(30) Foreign Application Priority Data

Mar. 31, 2014  (EP) .................................... 14162587

(51) Int. Cl.
| | | |
|---|---|---|
| *A61K 9/28* | (2006.01) | |
| *C07D 498/22* | (2006.01) | |
| *A61K 9/20* | (2006.01) | |
| *A61K 31/437* | (2006.01) | |

(52) U.S. Cl.
CPC .......... *C07D 498/22* (2013.01); *A61K 9/2095* (2013.01); *A61K 9/28* (2013.01); *A61K 9/2893* (2013.01); *A61K 31/437* (2013.01)

(58) Field of Classification Search
None
See application file for complete search history.

(56) References Cited

U.S. PATENT DOCUMENTS

| | | | |
|---|---|---|---|
| 4,341,785 A | 7/1982 | Marchi et al. | |
| 4,557,866 A | 12/1985 | Cannata et al. | |
| 6,861,053 B1 | 3/2005 | Lin et al. | |
| 7,045,620 B2 | 5/2006 | Viscomi et al. | |
| 7,452,857 B2 | 11/2008 | Lin et al. | |
| 7,605,240 B2 | 10/2009 | Lin et al. | |
| 7,612,199 B2 | 11/2009 | Viscomi et al. | |
| 7,709,634 B2 | 5/2010 | Kothakonda et al. | |
| 7,718,608 B2 | 5/2010 | Lin et al. | |
| 7,902,206 B2 | 3/2011 | Viscomi et al. | |
| 7,906,542 B2 | 3/2011 | Viscomi et al. | |
| 7,915,275 B2 | 3/2011 | Viscomi et al. | |
| 7,923,553 B2 | 4/2011 | Viscomi et al. | |
| 7,928,115 B2 | 4/2011 | Forbes et al. | |
| 7,935,799 B2 | 5/2011 | Lin et al. | |
| 8,067,429 B2 | 11/2011 | Gushurst et al. | |
| 8,158,644 B2 | 4/2012 | Viscomi et al. | |
| 8,158,781 B2 | 4/2012 | Viscomi et al. | |
| 8,173,801 B2 | 5/2012 | Viscomi et al. | |
| 8,193,196 B2 | 6/2012 | Viscomi et al. | |
| 8,217,054 B2 | 7/2012 | Maffei et al. | |
| 8,227,482 B1 | 7/2012 | Parent et al. | |
| 8,309,569 B2 | 11/2012 | Forbes et al. | |
| 8,404,704 B2 | 3/2013 | Viscomi et al. | |
| 8,486,956 B2 | 7/2013 | Gushurst et al. | |
| 8,507,517 B2 | 8/2013 | Parent et al. | |
| 8,513,275 B2 | 8/2013 | Wu et al. | |
| 8,518,949 B2 | 8/2013 | Viscomi et al. | |
| 8,569,326 B2 | 10/2013 | Gushurst et al. | |
| 8,633,234 B2 | 1/2014 | Rao et al. | |
| 8,642,573 B2 | 2/2014 | Forbes et al. | |
| 8,735,419 B2 | 5/2014 | Parent et al. | |
| 8,741,904 B2 | 6/2014 | Viscomi et al. | |
| 8,748,449 B2 | 6/2014 | Maffei et al. | |
| 8,759,513 B2 | 6/2014 | Venkatramana et al. | |
| 8,815,888 B2 | 8/2014 | Wu et al. | |

(Continued)

FOREIGN PATENT DOCUMENTS

| | | |
|---|---|---|
| CA | 1215976 A1 | 12/1986 |
| CA | 1218650 A | 3/1987 |

(Continued)

OTHER PUBLICATIONS

Office Action in U.S. Appl. No. 15/300,879, dated Feb. 8, 2018.
Restriction Requirement in U.S. Appl. No. 15/300,879, dated Sep. 7, 2017.
Final Office Action in U.S. Appl. No. 15/300,879, dated Jul. 3, 2018.
Advisory Action in U.S. Appl. No. 15/300,879, dated Nov. 28, 2018.
Office Action in U.S. Appl. No. 15/928,971, dated Nov. 14, 2019.
Office Action in U.S. Appl. No. 16/240,547 dated Sep. 18, 2019.
Statement of Grounds of Appeal, with auxiliary claim requests, in Opposition of EP2927235, dated Dec. 26, 2019.

(Continued)

*Primary Examiner* — Tigabu Kassa
(74) *Attorney, Agent, or Firm* — Troutman Pepper Hamilton Sanders LLP (Rochester)

(57) ABSTRACT

A Rifaximin polymorphic mixture of α/β form in a relative ratio of 85/15±3 and a process for its preparation. The polymorphic mixture of Rifaximin is for use as a medicament, in particular in the treatment of traveler's diarrhea and hepatic encephalopathy. A pharmaceutical composition comprises the polymorphic mixture of Rifaximin as active ingredient, in particular, a solid formulation, more in particular, a film coated tablet. A polymorphic form of crude wet rifaximin and of purified wet rifaximin their use are used as intermediates in a process for the preparation of Rifaximin polymorphic mixture of α/β form in a relative ratio of 85/15±3.

11 Claims, 17 Drawing Sheets

(56) References Cited

U.S. PATENT DOCUMENTS

| | | | |
|---|---|---|---|
| 8,829,017 B2 | 9/2014 | Forbes et al. |
| 8,835,452 B2 | 9/2014 | Viscomi et al. |
| 8,853,231 B2 | 10/2014 | Viscomi et al. |
| 8,877,770 B2 | 11/2014 | Vigano' et al. |
| 8,883,795 B2 | 11/2014 | Kothakonda et al. |
| 8,946,252 B2 | 2/2015 | Forbes et al. |
| 8,952,159 B2 | 2/2015 | Lavagna |
| 8,969,398 B2 | 3/2015 | Forbes |
| 9,018,225 B1 | 4/2015 | Hotha |
| 9,034,892 B2 | 5/2015 | Gushurst et al. |
| 9,133,217 B2 | 9/2015 | Parent et al. |
| 9,181,274 B2 | 11/2015 | Gushurst |
| 9,186,355 B2 | 11/2015 | Hotha |
| 9,271,968 B2 | 3/2016 | Viscomi et al. |
| 9,273,066 B2 | 3/2016 | Gushurst et al. |
| 9,421,195 B2 | 8/2016 | Forbes et al. |
| 9,629,828 B2 | 4/2017 | Forbes et al. |
| 2005/0101598 A1 | 5/2005 | Viscomi et al. |
| 2009/0082558 A1 | 3/2009 | Kothakonda et al. |
| 2015/0284407 A1 | 10/2015 | Blazecka et al. |
| 2017/0015682 A1 | 1/2017 | Grisenti et al. |
| 2020/0002356 A1 | 1/2020 | Grisenti et al. |

FOREIGN PATENT DOCUMENTS

| | | |
|---|---|---|
| EP | 0161534 B1 | 9/1989 |
| EP | 0616808 B1 | 9/1996 |
| EP | 0858804 B1 | 6/2002 |
| EP | 1557421 | 7/2005 |
| EP | 1676847 B1 | 7/2006 |
| EP | 1698630 | 9/2006 |
| EP | 1557421 B1 | 5/2007 |
| EP | 1676847 A1 | 1/2009 |
| EP | 1676848 B1 | 1/2009 |
| EP | 2208730 A1 | 7/2010 |
| EP | 2210893 A1 | 7/2010 |
| EP | 2069363 B1 | 3/2013 |
| EP | 1698630 B1 | 9/2014 |
| EP | 2927235 A1 | 10/2015 |
| EP | 3126367 A1 | 2/2017 |
| EP | 2059232 B1 | 4/2017 |
| ES | 2621557 T3 | 7/2017 |
| JP | 2008531623 A | 8/2008 |
| JP | 2011046738 A | 3/2011 |
| JP | 2013184902 A | 9/2013 |
| WO | WO 2005044823 A2 | 5/2005 |
| WO | WO 2006094662 A1 | 9/2006 |
| WO | WO 2008029208 A1 | 3/2008 |
| WO | WO 2008035109 A1 | 3/2008 |
| WO | WO 2008155728 A1 | 12/2008 |
| WO | WO 2009108730 | 9/2009 |
| WO | WO 2011153444 | 12/2011 |
| WO | WO 2012060675 A1 | 5/2012 |
| WO | WO 2012150561 A1 | 11/2012 |
| WO | WO 2012155981 A1 | 11/2012 |
| WO | WO 2012156533 A1 | 11/2012 |
| WO | WO 2012156951 A1 | 11/2012 |
| WO | WO 2013027227 A1 | 2/2013 |
| WO | WO 2015014984 A1 | 2/2015 |
| WO | WO 2015150171 A1 | 10/2015 |
| WO | WO 2015159275 A2 | 10/2015 |
| WO | WO 2015173697 A1 | 11/2015 |

OTHER PUBLICATIONS

Office Action in U.S. Appl. No. 15/140,167, dated Sep. 22, 2017.
Restriction Requirement in U.S. Appl. No. 15/140,167 dated Dec. 30, 2016.
Office Action in U.S. Appl. No. 15/140,235, dated Mar. 29, 2017.
Censi et al., "Polymorph Impact on the Bioavailability and Stability of Poorly Soluble Drugs," Molecules, 20(10):18759-776 (2015).
Blandizzi et al., "Is Generic Rifaximin Still a Poorly Absorbed Antibiotic? A Comparison of Branded and Generic Formulations in Healthy Volunteers," Pharmacological Research 85:39-44 (2014).
Harry Brittain, "Review: Polymorphism and Solvatomorphism 2008," Journal of Pharmaceutical Sciences 99(9):3648-664 (2010).
Cellai et al., "Structure-Activity Relationships in 4-deoxypyrido(1',2'-1.2)imidazo(5.4-c)rifamycin SV derivatives," Chemioterapia 2(5):53-54 (1983).
Viscomi et al., "Crystal Forms of Rifaximin and Their Effect on Pharmaceutical Properties," CrystEngComm 10:1074-81 (2008).
Guidance for Industry ANDAs: Pharmaceutical Solid Polymorphism Chemistry, Manufacturing, and Controls Information. U.S. Department of Health and Human Services Food and Drug Administration Center for Drug Evaluation and Research (CDER) (2007).
Viscomi, Declaration submitted to USPTO (U.S. Appl. No. 10/728,090, dated Jan. 17, 2006).
Bianchetti, Answer to EPO (ref. EP Patent App. No. 04 00 5541, dated May 2, 2006).
Stradi et al., "Structural Elucidation of the Rifaximin Ph. Eur. Impurity H," Journal of Pharmaceutical and Biomedical Analysis 51(4):858-65 (2010).
Final Office Action in U.S. Appl. No. 15/140,235 dated Dec. 7, 2017.
European Search Report for Application Serial No. 14162587.1 dated Jul. 21, 2014.
PCT International Preliminary Report on Patentability for International Application No. PCT/EP2015/056304 dated Oct. 4, 2016.
Notice of opposition of a European Patent No. EP2927235 B1 dated Nov. 8, 2017.
Normix: Certificate of Technical Characteristics (SmPC), Aug. 2009, with English translation.
Targaxan: www.medicine.org.uk Oct. 1, 2013.
Australian Public Assessment report Xifaxan, 2012.
Campbell Roberts et al., "Quantitative Analysis of Mannitol Polymorphs. X-ray powder Diffractometry—Exploring Preferred Orientation Effects," Journal of Pharmaceutical and Biomedical Analysis, 28:1149-1159 (2002).
Bobrovs et al., "Optimization of Sample Preparation Conditions for Detecting Trace Amounts of β-Tegafur in α- and β-Tegafur Mixture," J. Pharm. Sciences 101(12):4608-4614 (2012).
Gibson, ed. Pharmaceutical Preformulation and Formulation pp. 403-440 (2001).
Braga et al., "The Structure-Property Relationship of Four Crystal Forms of Rifaximin," CrystEngComm. 14:6404-6411 (2012).
Zevin et al., Mureinik ed. Quantitative X-Ray Diffractometry, New York, Springer-Verlag (1995).
Jenkins et al., "Quantitative Analysis", Introduction to X-Ray Powder Diffractometry, John Wiley & Sons Inc., pp. 355-361 (1996).
Shankland, "An Overview of Powder X-Ray Diffraction and Its Relevance to Pharmaceutical Crystal Structures," in Mullertz eds. Analytical Techniques in the Pharmaceutical Sciences (2016).
Kidd et al., "The Applicability of Powder X-Ray Diffraction to the Quantification of Drug Substance Polymorphs Using a Model Organic System," Powder Diffraction 8(3):180-187 (1993).
Declaration by Prof. Fabrizia Grepioni, dated Nov. 6, 2017.
Curriculum Vitae of Prof. Fabrizia Grepioni dated Oct. 30, 2017.
Comparison of Figure 2 of WO2009/108730 and Figure 2 of EP2927235.
Table corresponding to Annex 2, filed on Apr. 6, 2016, with alignment peaks.
Response to the Notice of Opposition of European Patent No. EP29277235 B1 dated Apr. 16, 2018.
"Characterization of Crystalline and Partially Crystalline Solids by X-ray Powder Diffraction," U.S. Pharmacopoeia National Formulary 1(941):692 and 697 (2015).
Dinnebier et al., "General Data Reduction," Powder Diffraction, Theory and Practice, RSC Publishing, Cambridge UK, p. 125 (2008).
Response to the Notice of Opposition of European Patent No. EP1557421 dated Sep. 10, 2008.
Dr. Sun's Affidavit in Response to Opposition of EP2929235 dated Apr. 16, 2018.
"Characterization of Crystalline and Partially Crystalline Solids by X-ray Powder Diffraction," U.S. Pharmacopoeial Convention (941):427-433 (2012).

(56) References Cited

OTHER PUBLICATIONS

International Search Report and Written Opinion dated May 21, 2015 issued in related application PCT/EP2015/056304.
Reply to the Summons to Attend Oral Proceedings of European Patent No. EP2927235 B1, mailed Dec. 12, 2018.
Manufacturer information sheet on SYLOID® 244 FP Silica from www.discoverysciences.com.
Rowe, R.C. eds, "Disodium Edetate," Handbook of Pharmaceutical Excipients, 6th Ed, London, Pharmaceutical Press, pp. 242-243 (2009).
Rowe, R.C. eds, "Polyvinyl Alcohol," Handbook of Pharmaceutical Excipients, 6th Ed, London, Pharmaceutical Press, pp. 564-565 (2009).
"ICH Harmonised Tripartite Guidelines Stability Testing of New Drug Substances and Products Q1A(R2)" from the International Conference on Harmonisation of Technical Requirements for Registration of Pharmaceuticals for Human Use, dated Feb. 6, 2003.
Annex to the Communication in the Opposition of EP2927235, dated Jul. 26, 2018.
Response to the summons to attend oral proceedings in the Opposition of EP 2927235, Dated Dec. 13, 2018.
Experimental Report in the Opposition of EP 2927235, Dated Dec. 13, 2018.
Curriculum Vitae of G. C. Viscomi in the Opposition of EP 2927235, Dated Dec. 13, 2018.
Reply to the Opponent's Written Submission in the Opposition of Ep 2927235, Dated Jan. 14, 2019.
List of Litigation Cases of Opponent in the Opposition of EP 2927235.
Restriction Requirement in U.S. Appl. No. 15/928,971 dated Jan. 11, 2019.
English translation of the Office Action in Japanese Patent Application No. 2016-559987, based on PCT/EP2015/056304, dated Nov. 27, 2018.
Communication in the Opposition of EP2927235, dated Jun. 26, 2019.
Declaration of Dr. D. Braga in the Opposition of EP2927235, dated Jun. 18, 2019.
Curriculum vitae et Studiorum of Prof. D. Braga (2019).
Reply to the opponent's written submission in the Opposition of EP2927235, dated Jul. 3, 2019.
Information about the result of the oral hearing for EP Application No. 14162587.1, dated Jul. 11,2019.
Minutes of the oral proceedings in the Opposition of EP2927235, dated Aug. 8, 2019.
Reason for the decision of the oral proceedings in the Opposition of EP2927235, dated Aug. 8, 2019.
Opposition Response to Grounds of Appeal in EP2927235, dated Apr. 24, 2020.
Pre-appeal Examination Report in JP Patent Application No. 2016-559987, based on PCT/EP2015/056304, dated Apr. 1, 2020, with English Translation.
Decision of Refusal in Japanese Application No. 2016-559987, based on PCT/EP2015/056304, dated Jul. 12, 2019, with English translation.
Office Action in Japanese Application No. 2019-212153, a divisional of Japanese Application No. 2016-559987, based on PCT/EP2015/056304, dated Dec. 8, 2020.
Office Action in Japanese Application No. 2016-559987, dated Jan. 12, 2021.

POLYMORPHIC MIXTURE OF RIFAXIMIN AND ITS USE FOR THE PREPARATION OF SOLID FORMULATIONS

CROSS REFERENCE TO RELATED APPLICATIONS

This application is a continuation of U.S. patent application Ser. No. 15/300,879, filed Sep. 30, 2016, which is now U.S. Pat. No. 10,556,915, which is the U.S. National Phase of International Application No. PCT/EP15/056304, filed on Mar. 24, 2015, and claims priority to European Application No. 14162587.1, filed on Mar. 31, 2014, the contents of each are incorporated by reference herein, in their entirety and for all purposes.

FIELD OF THE INVENTION

The present invention relates to the field of organic chemistry, in particular of medicinal chemistry, more in particular to the field of the manufacture of Active Pharmaceutical Ingredients (APIs).

BACKGROUND OF THE INVENTION

Rifaximin (compound identified by CAS registry number 80621-81-4) is a non-absorbable semisynthetic rifamycin antibiotic disclosed for the first time by Alfa Wasserman on 1981 (BE888895); this compound is currently utilized in therapy for the treatment of traveler's diarrhea and hepatic encephalopathy. Pharmacokinetics studies carried out on Rifaximin confirmed that this compound is not absorbed from the intestine to any significant amount (Cellai, L.; Cerrini, S.; Brufani, M.; Marchi, E.; Mascellani, G.; Montecchi, L. Structure-activity relationships in 4-deoxypyrido (1',2'-1.2)imidazo(5.4-c) rifamycin SV derivatives. Chemioterapia (1983), 2(5. Suppl.: Mediterr. Congr. Chemother., Proc., 3rd, 1982), 53-4).

The structural formula of Rifaximin is the following

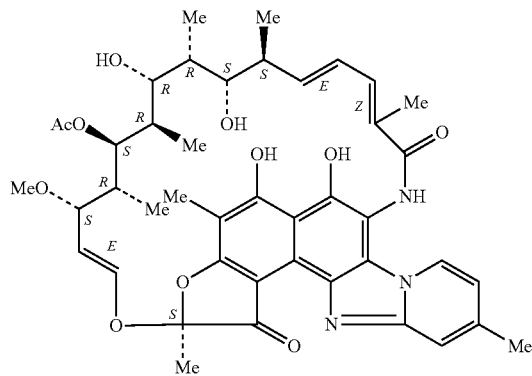

Due to this lack of systemic absorption Rifaximin has no application outside the gastrointestinal tract and has an excellent safety profile.

Literature data confirm that this substance may be isolated in different crystalline forms identified with the letters of the Greek alphabet: the α, β, and γ forms were disclosed on 2004 (EP1557421 by Alfa Wasserman), the ε and δ forms on 2006 (EP1698630 by Alfa Wasserman), the ζ, η, α dry, ι forms on 2009 (WO2009108730 by Salix Pharmaceuticals, Ltd.), K and Θ forms on 2011 (WO2011153444 by Salix Pharmaceuticals, Ltd.). Moreover it is known that Rifaximin may exist in an amorphous form (WO2008035109 by Cipla Limited) and in an amorphous halo form (WO2011080691).

Rifaximin in the polymorphic form α (the crystalline form present on the market with the trade name of Xifaxan®) is considered a non-absorbable drug, however the results of more recent pharmacological studies (see for example G. C. Viscomi et al. Crystal forms of Rifaximin and their effect on pharmaceutical properties Cryst Eng Comm, 2008. 10. 1074-1081) suggest that some of the above listed crystalline forms, for example the γ and the δ forms could be significantly absorbed.

Moreover, the above cited literature data indicate that the known polymorphic forms of Rifaximin may easily change their polymorphic form if exposed to different values of relative humidity: for example the anhydrous α- and δ-forms can be obtained by drying the monohydrate β-form at different temperatures (30-65° C.) under vacuum and the anhydrous α form can be transformed into the corresponding monohydrate β form at a relative humidity of 56% after 40 hours (EP 1557421).

The present inventors found that in particular the crystallization and drying conditions (using traditional static or dynamic drier, like a biconical drier) described in EP 1557421 showed to be critical since they did not consistently afford the desired α or α/β mixtures but the undesired γ polymorphic form or other polymorphic mixtures.

The control of the obtained solid state of Rifaximin polymorphic forms is usually performed by DRX spectroscopy, since the traditional differential calorimetry analysis (DSC) and infrared spectroscopy (IR) are not able to discriminate and to quantify these polymorphs; also the water content, as determined by Karl-Fisher, can give only indirect information on the solid state since cannot discriminate between adsorbed water and water in the lattice. Moreover, more than one hydrate and anhydrous forms for Rifaximin have been described.

The conversion of these polymorphic forms is therefore critical and need to be taken into account in order to guarantee the "consistency" of the crystalline form in the Active Pharmaceutical Ingredient (API) and in the drug product (Guidance for Industry ANDAs: Pharmaceutical Solid Polymorphism Chemistry, Manufacturing, and Controls Information. U.S. Department of Health and Human Services Food and Drug Administration Center for Drug Evaluation and Research (CDER) July 2007).

It should be pointed out that the "consistency", namely the reproducibility of the polymorphic form, is very important, especially in view of the regulatory requirements.

Finally, also for the preparation of the drug product the stability of the polymorphic forms of Rifaximin (for example film coated tablets) is critical. The present inventors have experimental evidence that the wet granulation procedures and tableting might modify the initial solid state of this API: for example the wet granulation procedure of Rifaximin α form, a procedure that provides the use of purified water as binding agent, afforded a sensible amount of Rifaximin β form (<50%) as result of a change in the solid state of this API from anhydrous (α form) to hydrate (β form).

These findings indicate the need of putting appropriate manufacturing procedures in place to consistently yield Rifaximin of the appropriate solid state suitable to minimize changes of the solid state during the preparation of the drug product.

SUMMARY OF THE INVENTION

It has now surprisingly been found that a new Rifaximin form, consisting of α/β mixture in a relative ratio of 85/15±3 can be prepared consistently solving the problems of the prior art as discussed above.

It has also been found a process for the preparation of a consistent Rifaximin α/β mixture in a relative ratio of 85/15±3 by crystallization and drying of a new polymorphic form of Rifaximin (hereinafter also named purified wet Rifaximin). Unexpectedly, this Rifaximin 85/15±3 α/β mixture is stable towards the influence of physical treatments employed for the dry granulation and tableting.

The preparation of this consistent mixture Rifaximin α/β is obtained through a drying procedure performed at 40° C. under nitrogen and under stirring at atmospheric pressure of a new mixture of polymorphic forms. Rifaximin α/β mixture in a relative ratio of 85/15±3 obtained through the above described process can be utilized to prepare film coated tablets using a dry granulation and tableting procedure without sensible modification of the relative ratio between the α and β polymorphic form.

Therefore, it is an object of the present invention a Rifaximin polymorphic mixture of α/β form in a relative ratio of 85/15±3.

Another object of the present invention is a process for the preparation of said Rifaximin polymorphic mixture of α/β form in a relative ratio of 85/15±3.

Another object of the present invention is a pharmaceutical composition, in particular a solid formulation, comprising the above polymorphic mixture of Rifaximin as active ingredient.

An object of the present invention is a film coated tablet comprising the above Rifaximin polymorphic together with a process for the preparation of said film coated tablet.

Another object of the present invention is the above polymorphic mixture of Rifaximin for use as a medicament, in particular in the treatment of traveler's diarrhea and hepatic encephalopathy Another object of the present invention is a polymorphic form of crude wet rifaximin obtained as intermediate in the process for the preparation of the above Rifaximin polymorphic mixture of α/β form in a relative ratio of 85/15±3.

Another object of the present invention is a polymorphic form of purified wet rifaximin obtained as intermediate in the process for the preparation of the above Rifaximin polymorphic mixture of α/β form in a relative ratio of 85/15±3.

Another object of the present invention is the use of the above crude wet rifaximin and/or of the above purified wet rifaximin as intermediate in a process for the preparation of Rifaximin polymorphic mixture of α/β form in a relative ratio of 85/15±3.

These and other objects of the present invention will be disclosed in the detail in the following also by means of Figures and Examples.

DETAILED DESCRIPTION OF THE INVENTION

Figure 1:
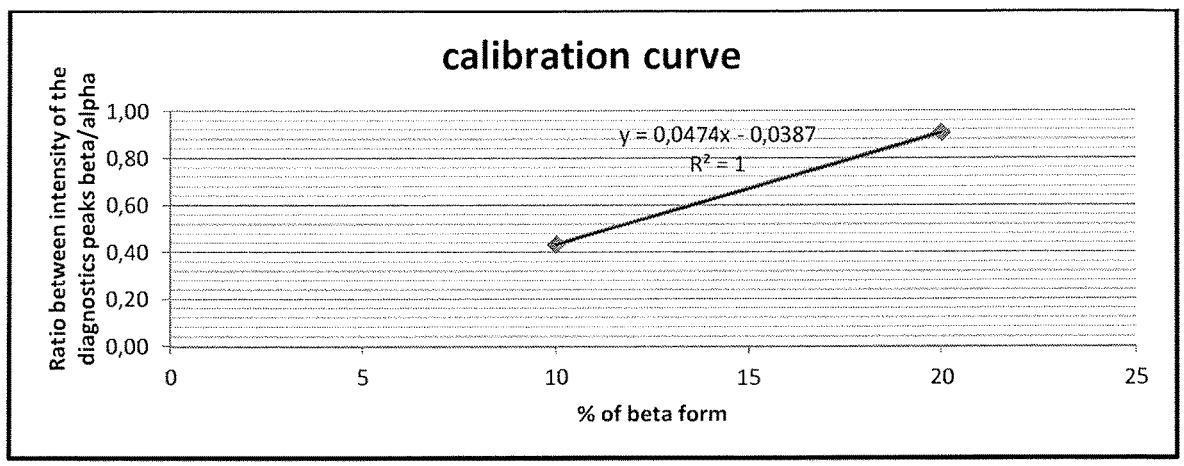
FIG. 1. Is a Calibration curve obtained using standard mixture of alpha and beta forms FIG. 2. Is a DRX of wet Rifaximin before crystallization FIG. 3. Is a DRX of wet Rifaximin: product recovered on the filter drier before drying FIG. 4. Is a DRX of Rifaximin α/β polymorphic mixture in a relative ratio of 85/15±3

Within the frame of the present invention we define "polymorphism" the ability of a solid material to exist in multiple forms or crystal structures known as polymorphs.

Within the frame of the present invention the terms "consistency" and "consistent" are used as synonyms of "reproducibility" and "reproducible". These terms are well understood by the person of ordinary skill in the art, in particular of the manufacture of APIs, also in view of the requirements of Regulatory Authorities.

According to the present invention, the process for the preparation of Rifaximin α/β polymorphic mixture in a relative ratio of 85/15±3 comprises the following steps:

a) reacting a molar equivalent of Rifamycin O with 2 or 3 equivalents of 2-amino-4-methylpyridine in a solvent mixture of water and ethyl alcohol in a volumetric ratio between 1:2 and 1:3, at a temperature between 20° C. and 30° C., to give a reaction mass;

b) treating said reaction mass at 20-30° C. with ascorbic acid, then with a mixture of water and ethyl alcohol and concentrated aqueous hydrochloric acid, adjusting pH of the reaction mass to a final value of 6.0-6.5, to obtain a suspension;

c) filtering the suspension, washing the resulting solid with a water/ethyl alcohol solvent mixture to obtain crude wet Rifaximin;

d) purifying crude wet Rifaximin by dissolving it in ethyl alcohol at a temperature between 50° C. and 60° C. and precipitating wet purified Rifaximin by adding water and by lowering the temperature of the suspension to between 28-33° C. under stirring for a period of time between 1-3 hours, cooling down the crystallization mixture to 20-25° C. under stirring for a period of time comprised between 1 and 2 hours and finally cooling down the crystallization mixture to 0-5° C. under stirring for a period of time to obtain a precipitate;

e) filtering the suspension on a filter drier, washing the resulting solid with water, and f) drying under stirring, under a inert gas flow at normal pressure, at a temperature comprised between 38 and 42° C. for a period of time to reach a final water content of 6±2%.

It is understood that all the values and intervals disclosed in the process of the present invention must not be intended as absolute. Any value or interval must be understood by the person of ordinary skill in the art as "about". The term "about", as currently intended, means that any value herein disclosed not necessarily must be exactly taken per se, but that a deviation from this value is within the scope of the present invention, provided that the technical effect herein disclosed is achieved.

In a preferred embodiment of the process according to the present invention, the concentration of rifamycin O in step a) is comprised between 0.2 and 0.4 M, the relative ratio between water and ethyl alcohol is 1:2.3 and the temperature of reaction is of 23° C.

Preferably, the molar equivalent of ascorbic acid with respect to the initial amount of rifamycin O in step b) is comprised in a range of 1/8 to 1/10. The relative ratio between water and ethyl alcohol is comprised in a range of 65/35 to 60/40 and the final concentration of hydrochloric acid is comprised between 2.5M and 3.5M.

Preferably, the relative ratio between the initial amount of Rifamycin O and the filter surface of the filter drier in the step e) is comprised between 1 g/0.6 cm$^2$ and 1 g/1.57 cm$^2$ Preferably, the stirring rate in step f) is of about 15 rpm/minute and the preferred temperature is of 40° C. and the drying time can be typically maintained for a time interval ranging from 20 to 25 hours, more preferably from about 21 hours. Preferably the inert gas of step f) is nitrogen.

The step f) can be optionally performed in a discontinuous way without affecting the relative ratio of the obtained polymorphic forms of Rifaximin.

Figure 2:
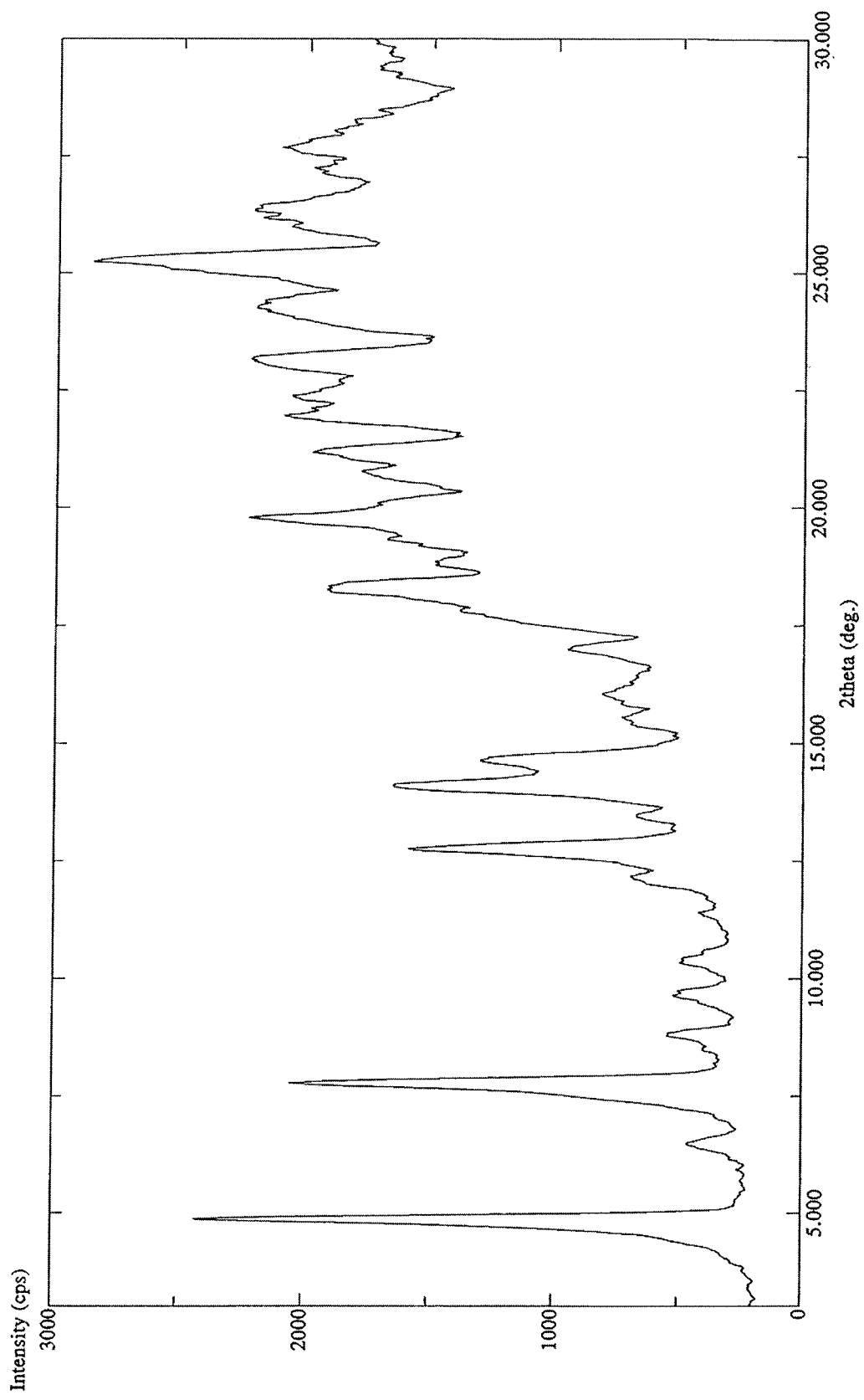

The crude wet Rifaximin recovered from step c) according to the present invention is characterized by an X-Ray spectrum with characteristic 2theta values at (relative intensity): 4.88 (87%), 7.78 (74%), 12.76 (57%), 14.08 (59%), 14.66 (46%), 17.80 (50%), 18.34 (69%), 19.78 (80%), 21.22 (70%), 21.92 (74%), 23.18 (80%), 25.30 (100%) (FIG. 2).

Figure 3:
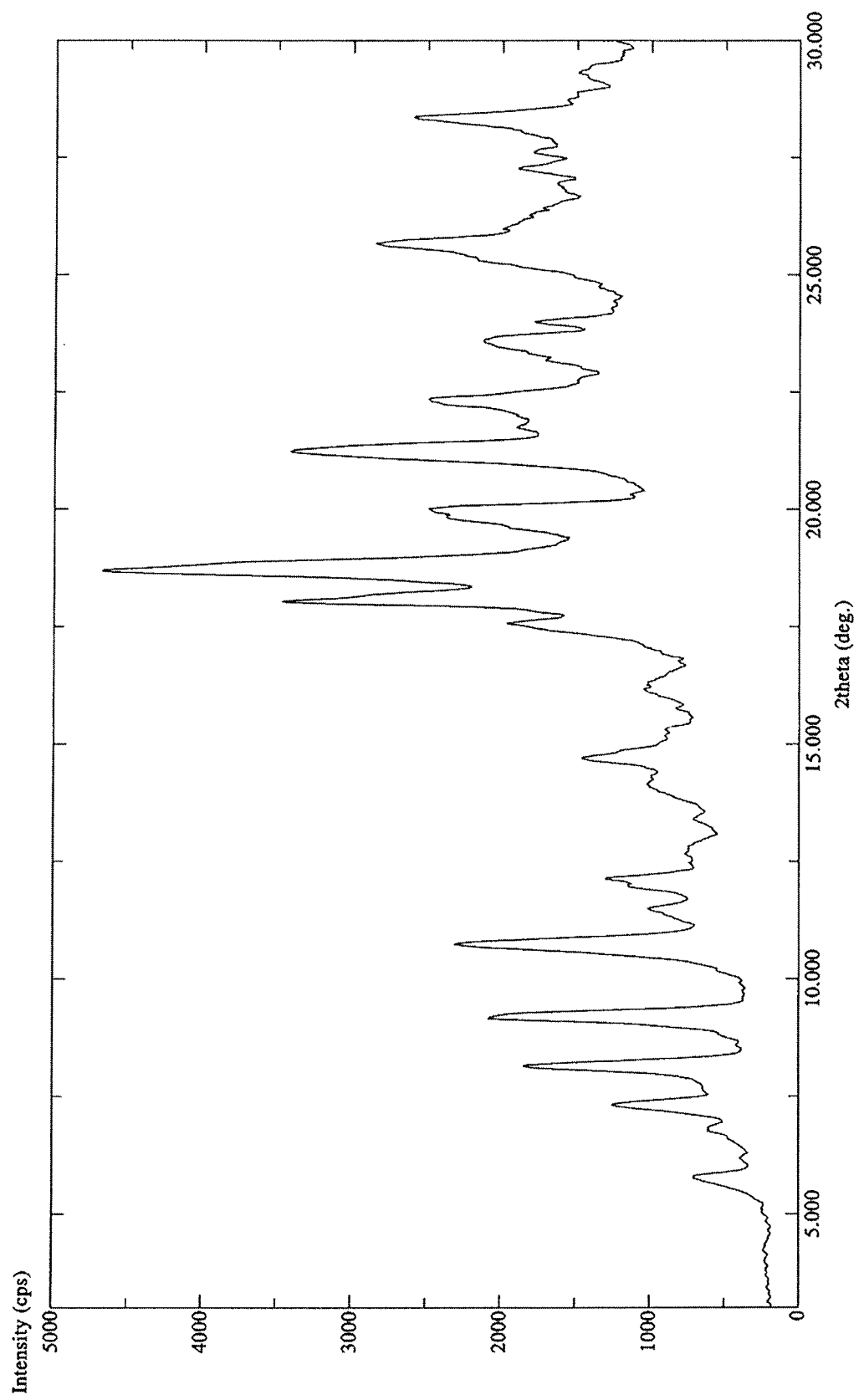

The purified wet Rifaximin recovered from step e) according to the present invention is characterized by an X-Ray spectrum with characteristic 2theta values at (relative intensity): 5.78 (15%), 7.32 (27%), 8.16 (40%), 9.20 (44%), 10.74 (50%), 17.56 (42%), 18.04 (75%), 18.70 (100%), 20.02 (54%), 21.24 (73%), 22.32 (54%), 23.62 (46%), 25.66 (61%) (FIG. 3).

Figure 4:
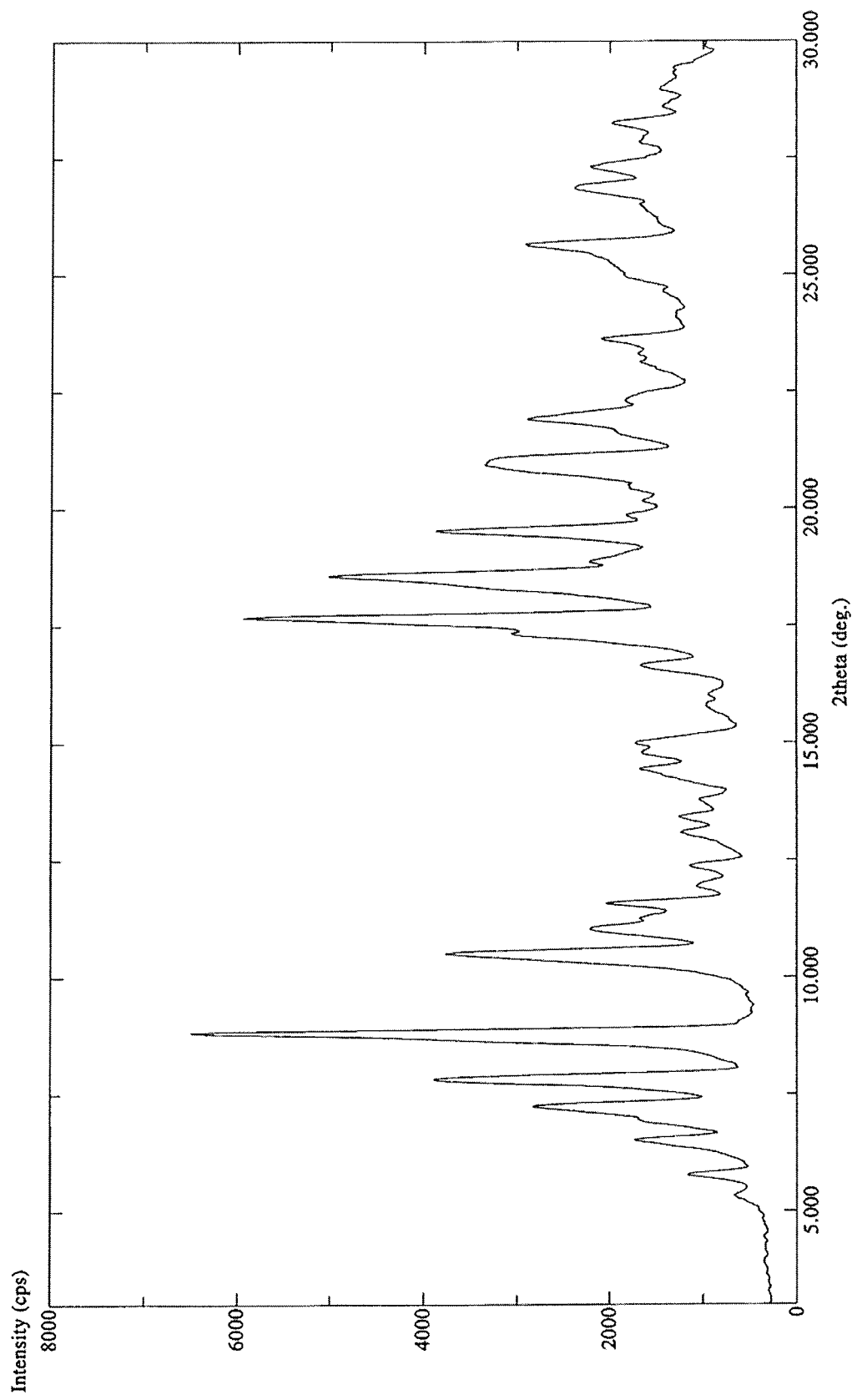

The Rifaximin α/β polymorphic mixture 85/15±3 recovered from step f) according to the present invention is characterized by an X-Ray spectrum with characteristic 2theta values at (relative intensity): 5.32 (11%), 5.78 (19%), 6.50 (27%), 7.24 (45%), 7.82 (61%), 8.80 (100%), 10.50 (59%), 11.02 (35%), 11.58 (32%), 13.08 (20%), 14.42 (26%), 17.32 (48%), 17.68 (93%), 18.58 (79%), 19.52 (61%), 21.04 (52%), 21.60 (30%), 21.92 (46%) (FIG. 4).

Generally, in the process according to the present invention, Rifamycin O is dispersed in a mixture of demineralized water and ethyl alcohol in the proportions above disclosed under stirring at 20-30° C., then 2-amino-4-methylpyridine was loaded. The reaction mixture is maintained under stirring for a sufficient time to let the reaction, preferably for 20-25 hours at 20-25° C.

After this period, L-ascorbic acid is added to the reaction mixture and the pH corrected under stirring at 20-30° C. to a final value of 6.0-6.5 by addition of 3M HCI in a water/ethanol solution (for example 62/38 v/v). The reaction mixture is then cooled down at 8-12° C. maintained under stirring for a time sufficient to obtain a massive precipitation, usually 2 hours, and filtered the suspension on a Büchner (or other equivalent) filter. The solid recovered on the filter was washed with an ethanol/water mixture, for example 1/1 v/v and utilized as such in the next step of crystallization.

The wet product recovered in the previous step is then dispersed in ethanol and heated under stirring until a solution is obtained. Conveniently, heating is around 50-60° C. Subsequently, water is added maintaining the heating temperature, conveniently around at 50-60° C. The reaction mixture is cooled down to 28-33° C. to afford a precipitate. The obtained suspension is maintained at 28-33° C. under stirring for 2 hours, then cooled down at 20-25° C. and stirred at this temperature for 1 hour and finally to 0-5° C. and stirred at this temperature for a time necessary to obtain a massive precipitate, usually 1 hour. The obtained suspension is filtered and the solid so recovered washed with water.

The purified wet Rifaximin recovered on the filter (new polymorphic form defined by characteristic DRX (powder) spectrum; FIG. 3) is dried under stirring at the temperature of 40° C. and under an inert gas flow (for example for 21 hours) to reach a water content of 6.0±2% (determined by Karl Fisher). Rifaximin as α/β polymorphic mixture with a relative ratio of 85/15±3 is so obtained.

The process according to the present invention shows advantageous consistency, affording the same polymorphic mixture with a variability of ±3% (from 82/18 to 88/12 of α/β polymorphic mixture) after a number of repetitions.

Advantageously, the α/β polymorphic mixture obtained by the process of the present invention is stable when stored at room temperature up to 6 months.

The Rifaximin mixture disclosed in the present invention is very useful in the preparation of pharmaceutical compositions containing it as active ingredient.

Said compositions comprise any of conventional vehicles, excipients, formulative ingredients and can be prepared according to the general knowledge in this art. A general reference can be found for example in Remington "The Science and Practice of Pharmacy, 21st edition Pharmaceutical Press.

In a preferred embodiment of the present invention, the Rifaximin mixture above disclosed is useful for the preparation of a film coated tablet.

Said compositions can be prepared according to the general knowledge in this art. A general reference can be found for example in Pharmaceutical Manufacturing Handbook: Production and Processes, Shayne Cox Gad, John Wiley & Sons, 2008.

Said compositions comprise any of conventional vehicles, excipients, formulative ingredients used in the technology of coating of solid pharmaceutical compositions, for example talc, microcrystalline cellulose, glycerol palmitostearate, sodium starch glycolate, hydrate silicon dioxide.

Accordingly, it is another object of the present invention a process for the preparation of a film coated tablet comprising the following steps:

a') mixing Rifaximin α/β polymorphic mixture in a relative ratio of 85/15±3 with suitable excipients at room temperature to give a an homogeneous mixture;

b') processing said mixture from step a') with dry granulation/compaction and sieving it on a 20 mesh sieve to obtain a blend;

c') compressing the blend obtained at step b') to afford tablets with a disintegration time in purified water at 37° C. of 1'20"±15";

d') coating the tablets obtained in step c') using suitable coating agents, plasticizers and opacifiers.

The step a') can be realized preferably utilizing excipients like microcrystalline cellulose, sodium starch glycolate, glycerol palmitostearate, hydrated silicon dioxide and talc in a relative ratio ranging from 33±3%, 4±0.4%, 4.9±0.5%, 0.5±0.05% and 3.0±0.3%

The step d') can be realized preferably utilizing coating agents like polyvinyl alcohol or hydroxypropyl methyl cellulose, plasticizers like polyethylene glycol, dibutyl sebacate, citrate esters, triacetin and opacifiers like titanium dioxide and aluminum lacquers more preferably polyvinyl alcohol, polyethylene glycol and titanium dioxide.

Figure 5:
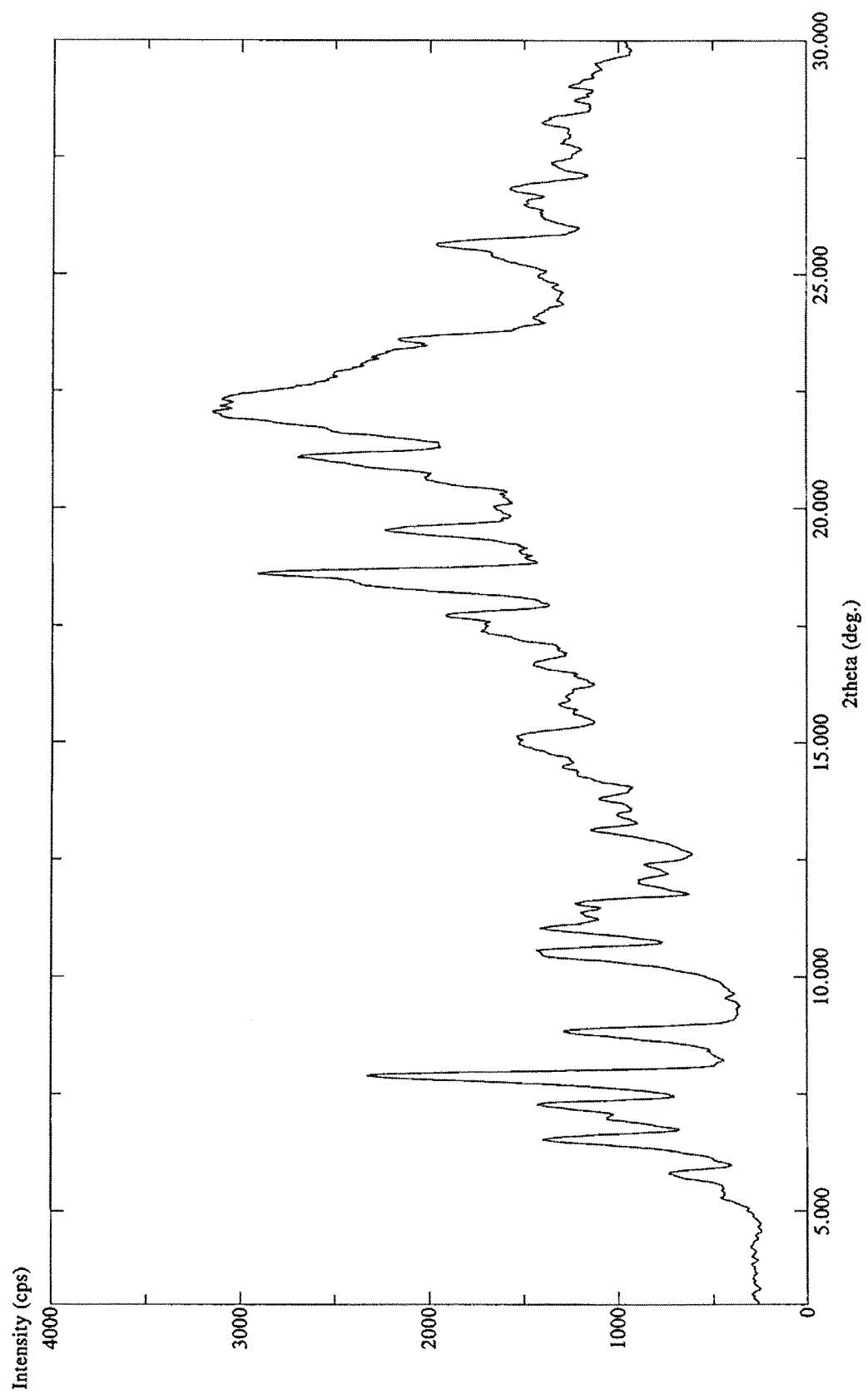
FIG. 5. Is a DRX of uncoated tablets of Rifaximin (dry granulation and compaction)
Figure 6:
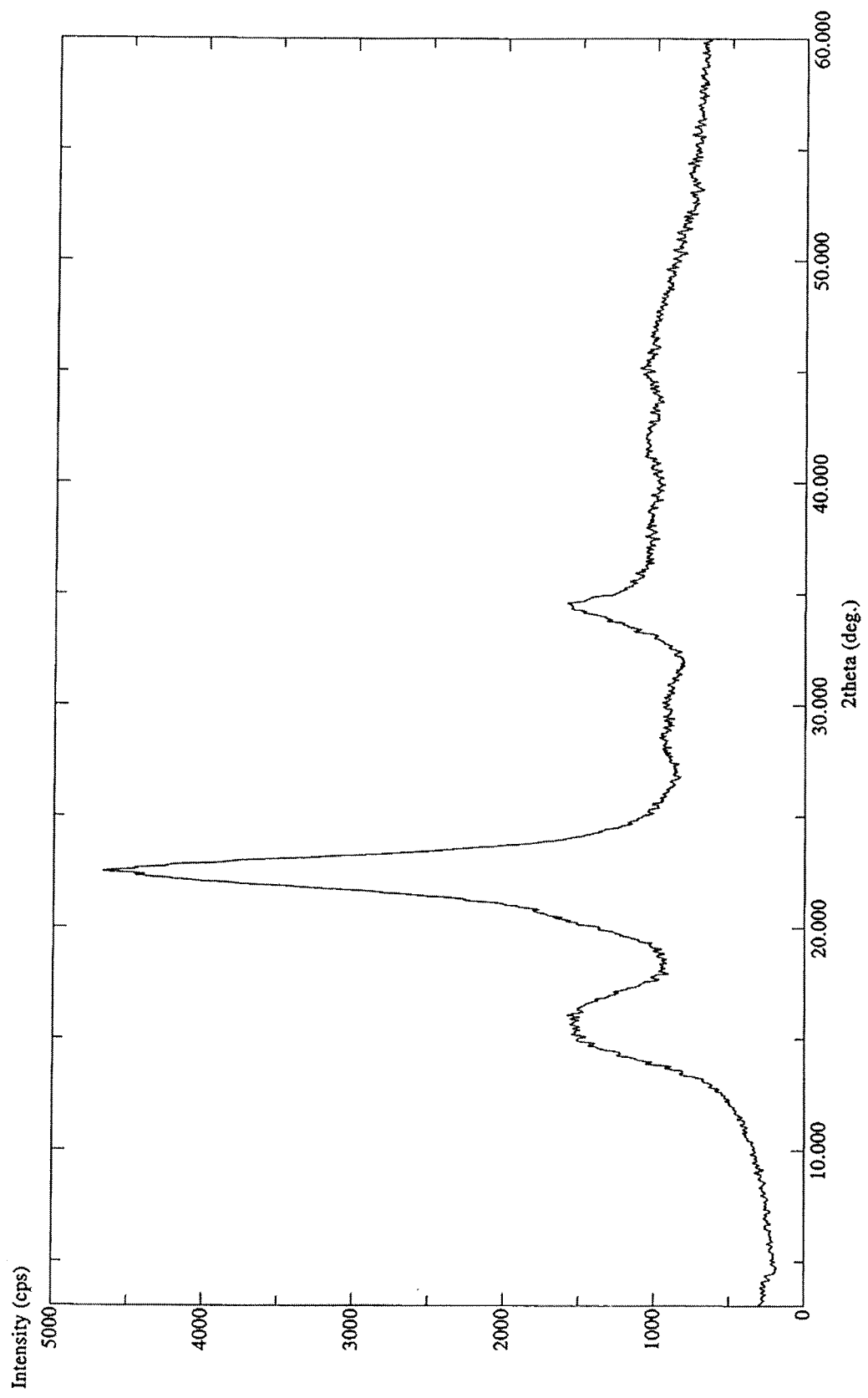
FIG. 6. Is a DRX of Cellulose Microcrystalline
Figure 7:
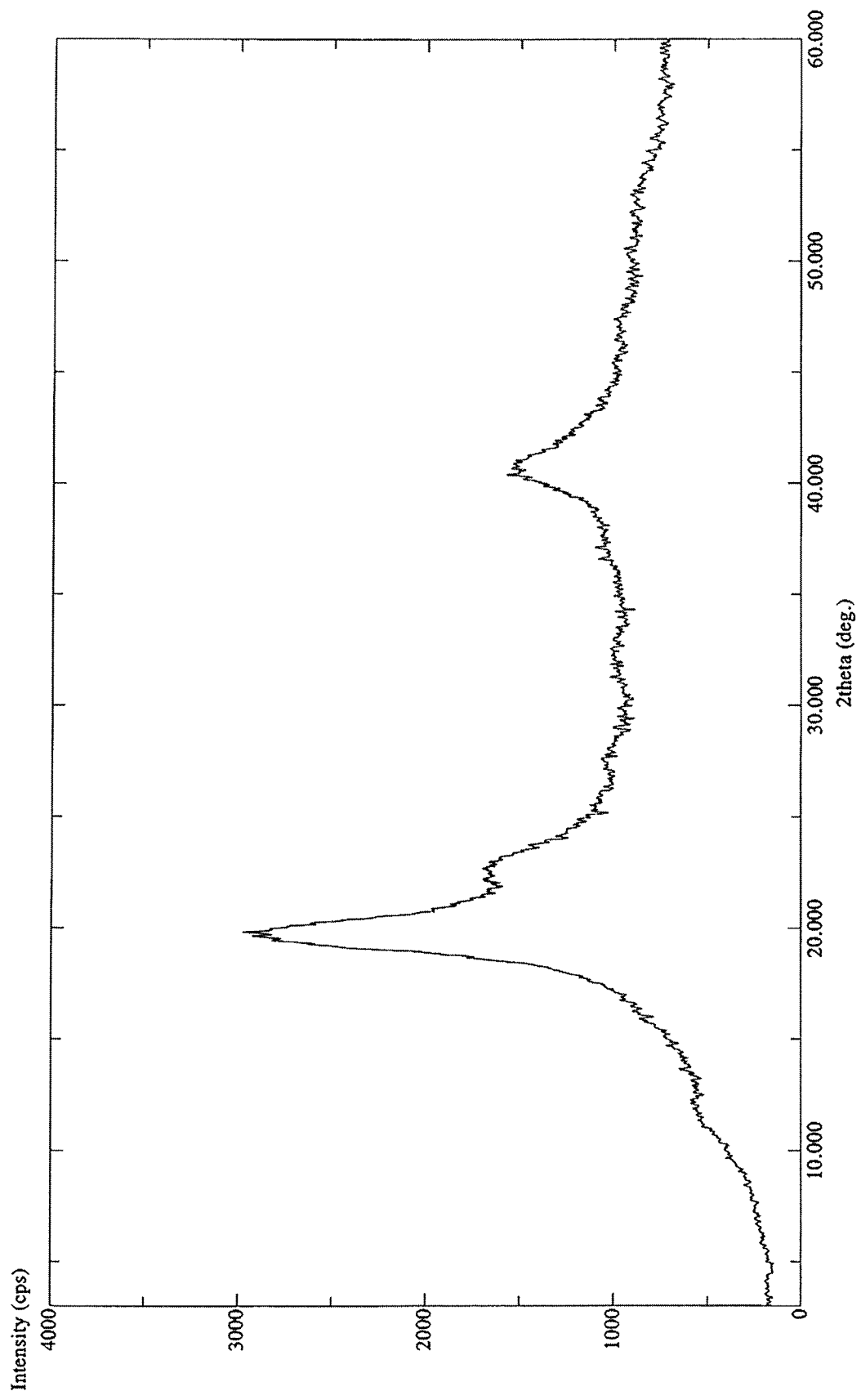
FIG. 7. Is a DRX of Polyvinyl Alcohol
Figure 8:
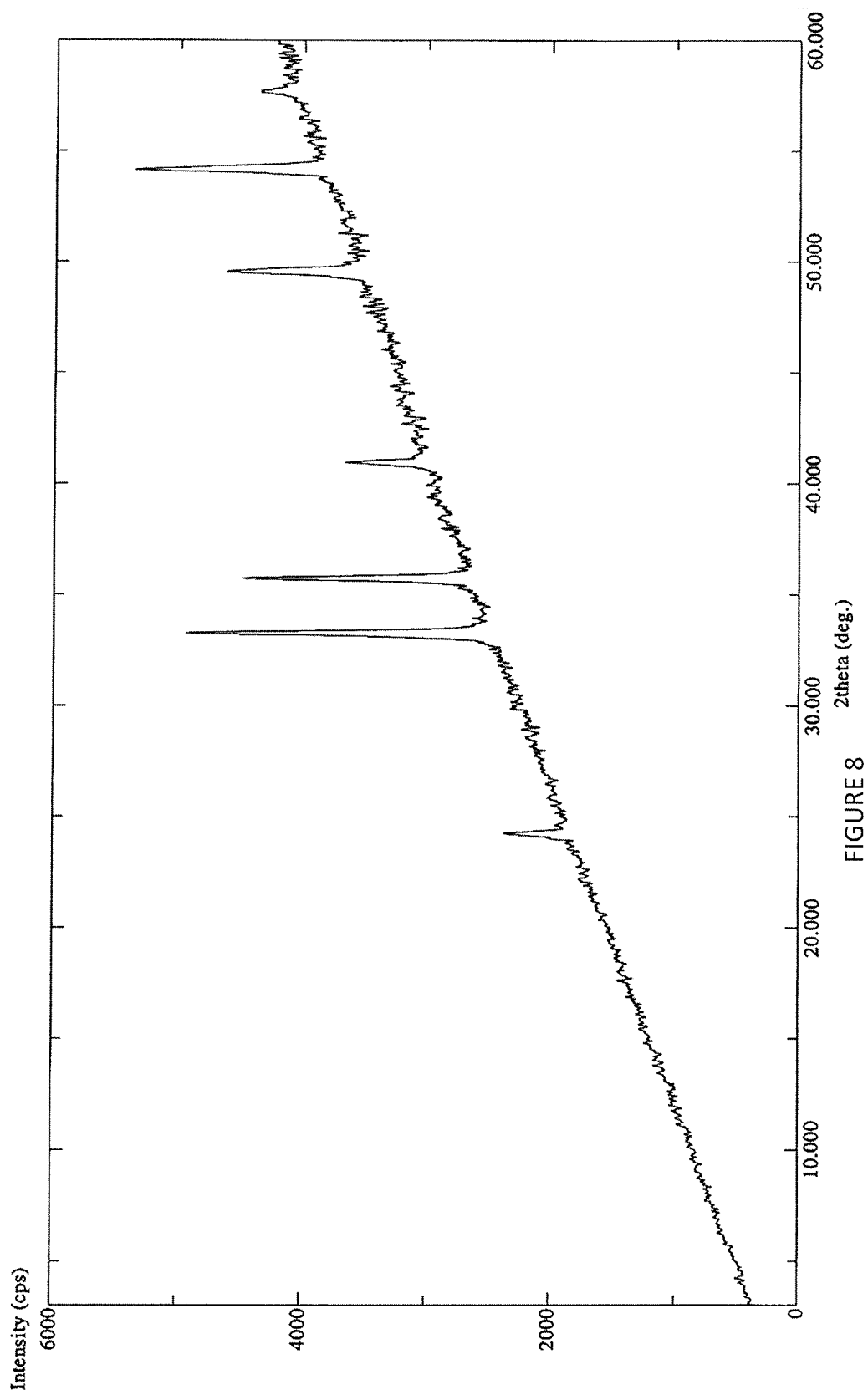
FIG. 8. Is a DRX of FeO (red iron oxide)
Figure 9:
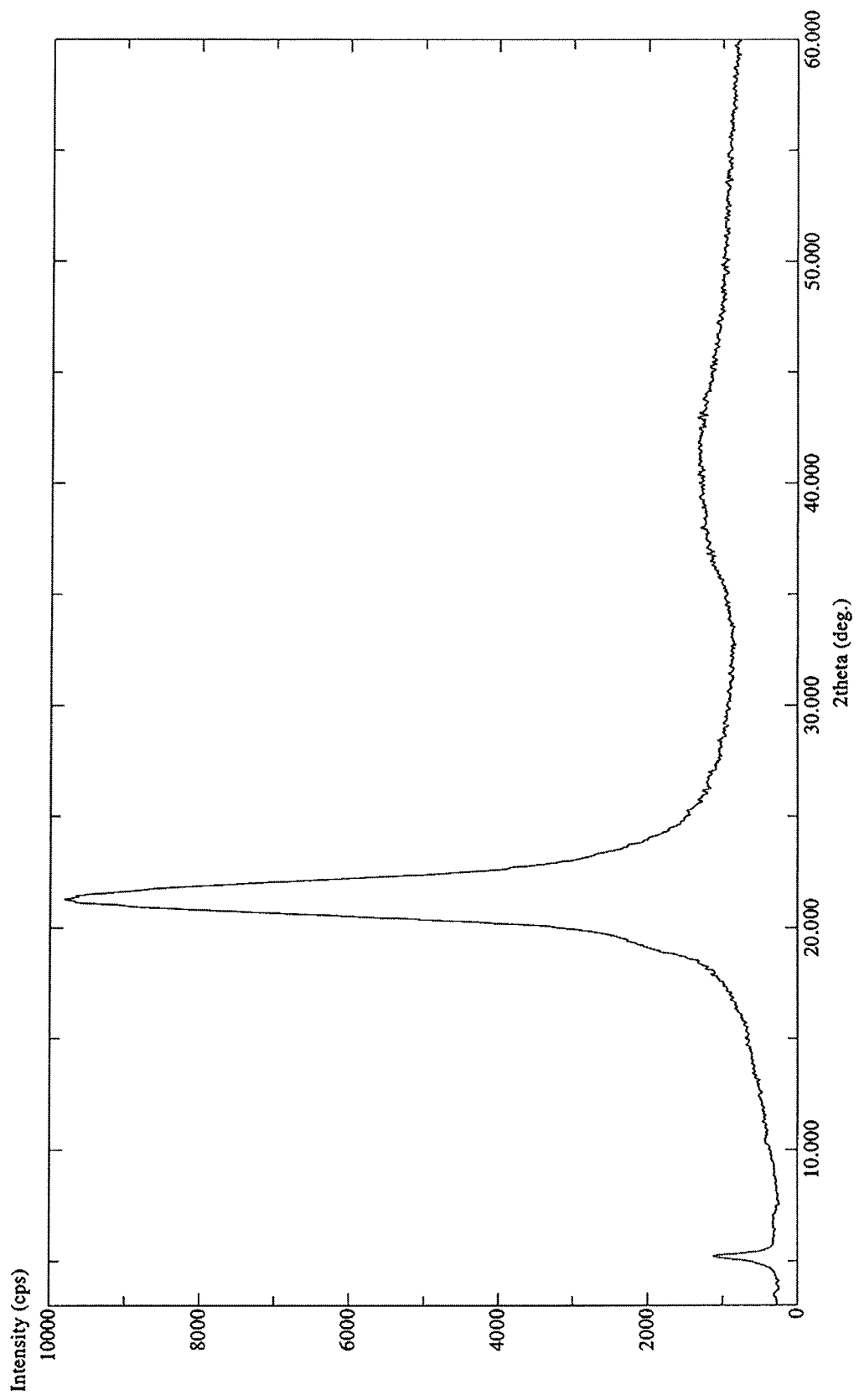
FIG. 9. Is a DRX of Gliceryl palmitostearate
Figure 10:
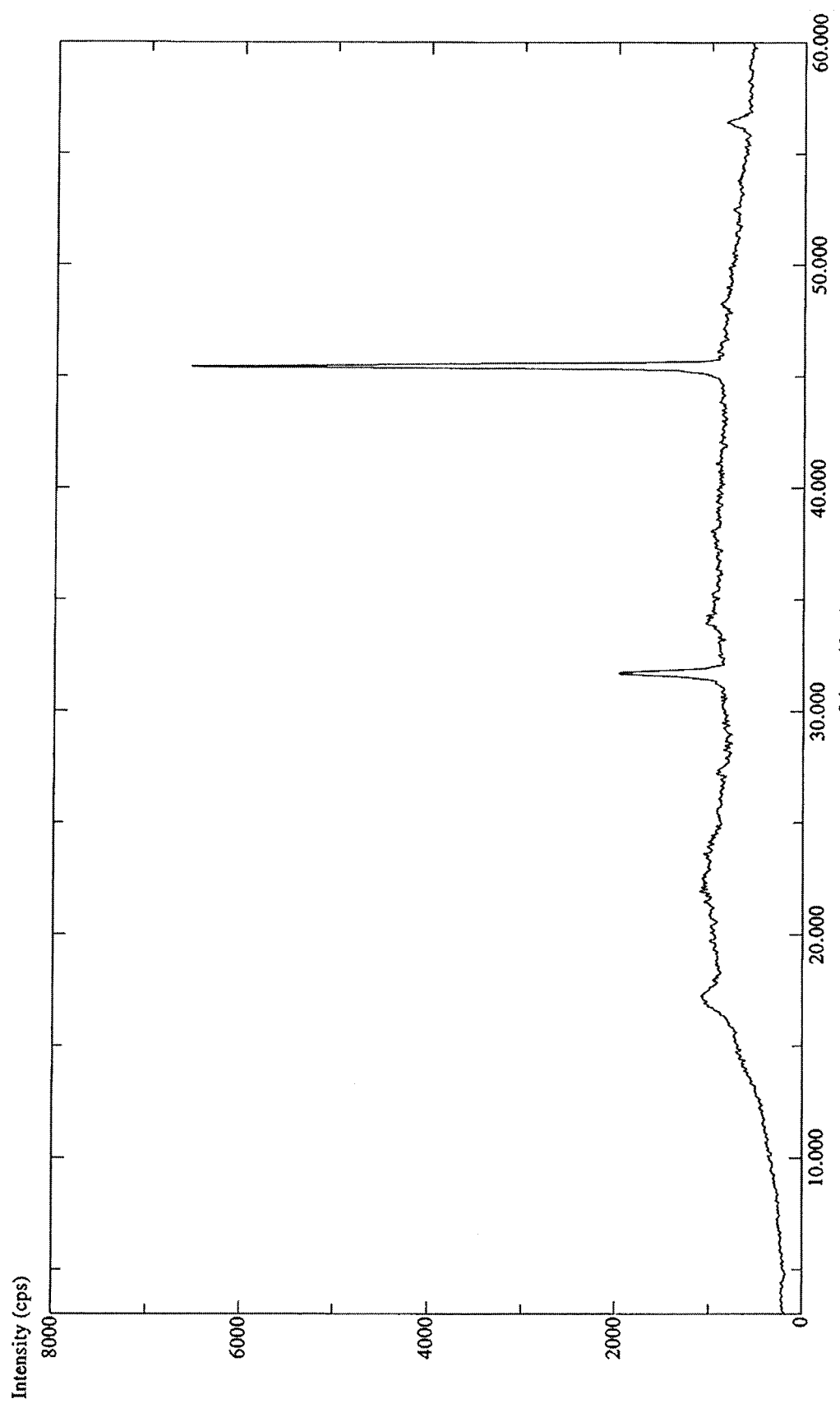
FIG. 10. Is a DRX of Sodium starch glycolate
Figure 11:
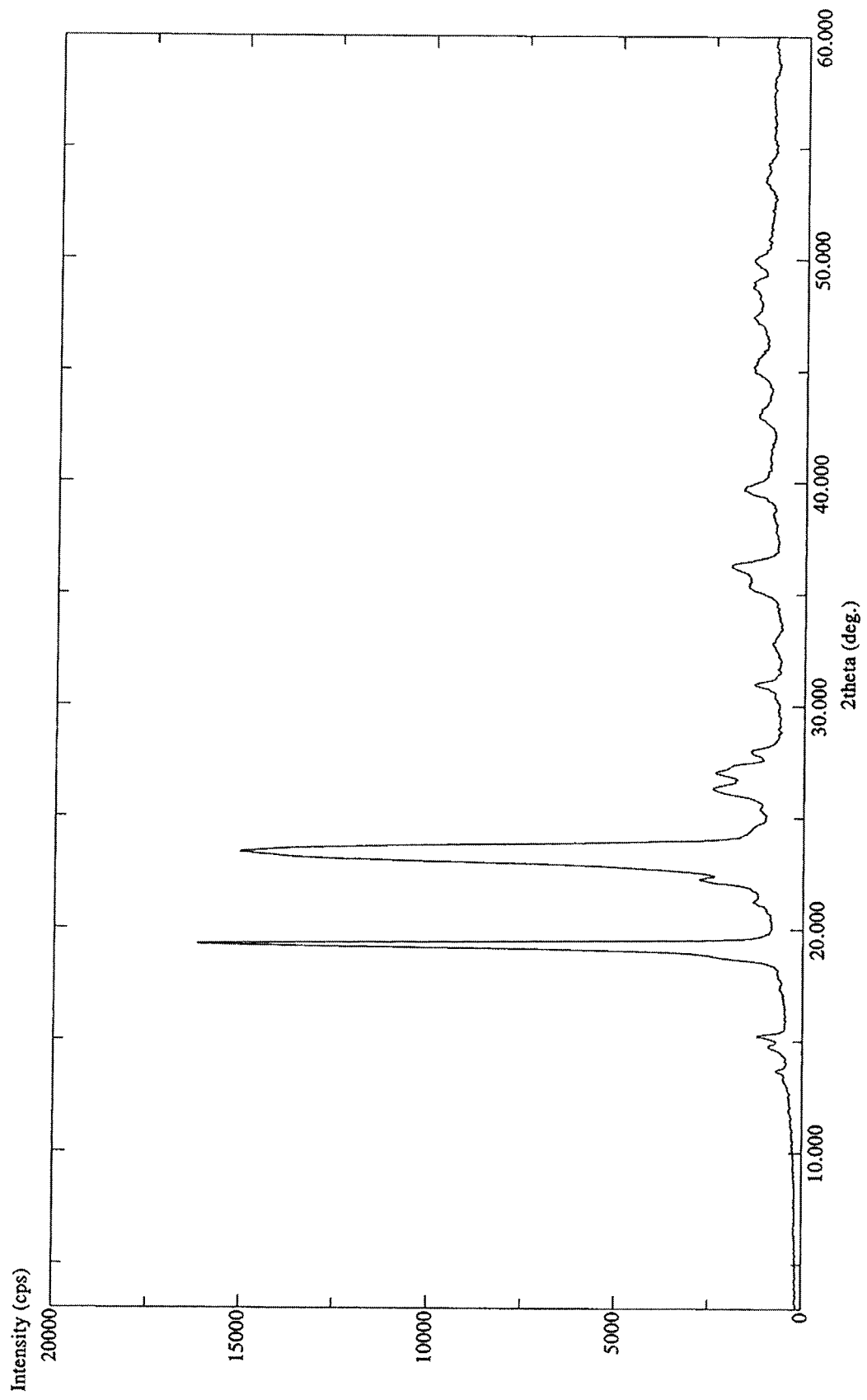
FIG. 11. Is a DRX of Polyethylene glycol 6000
Figure 12:
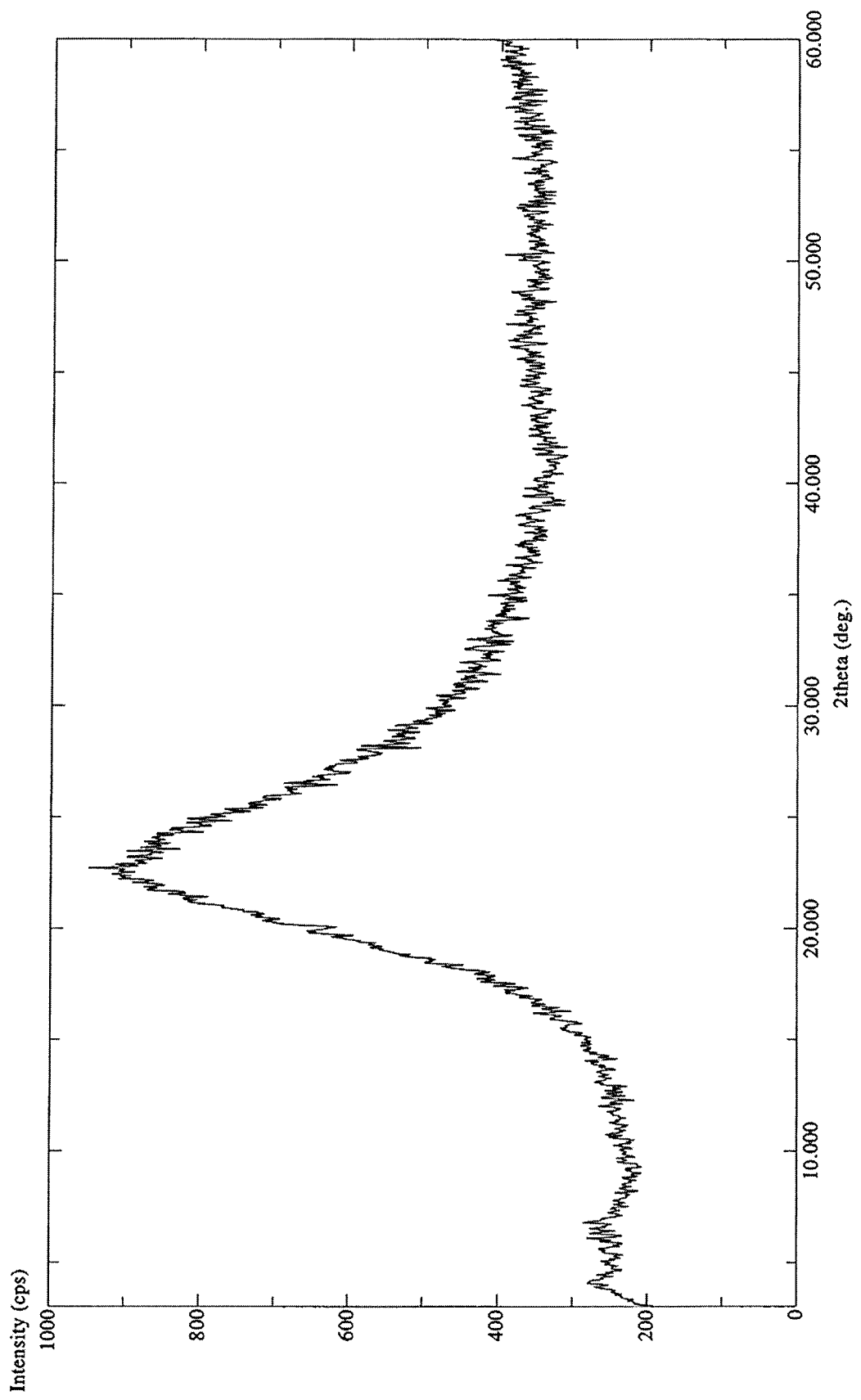
FIG. 12. Is a DRX of Hydrated Silicon Dioxide
Figure 13:
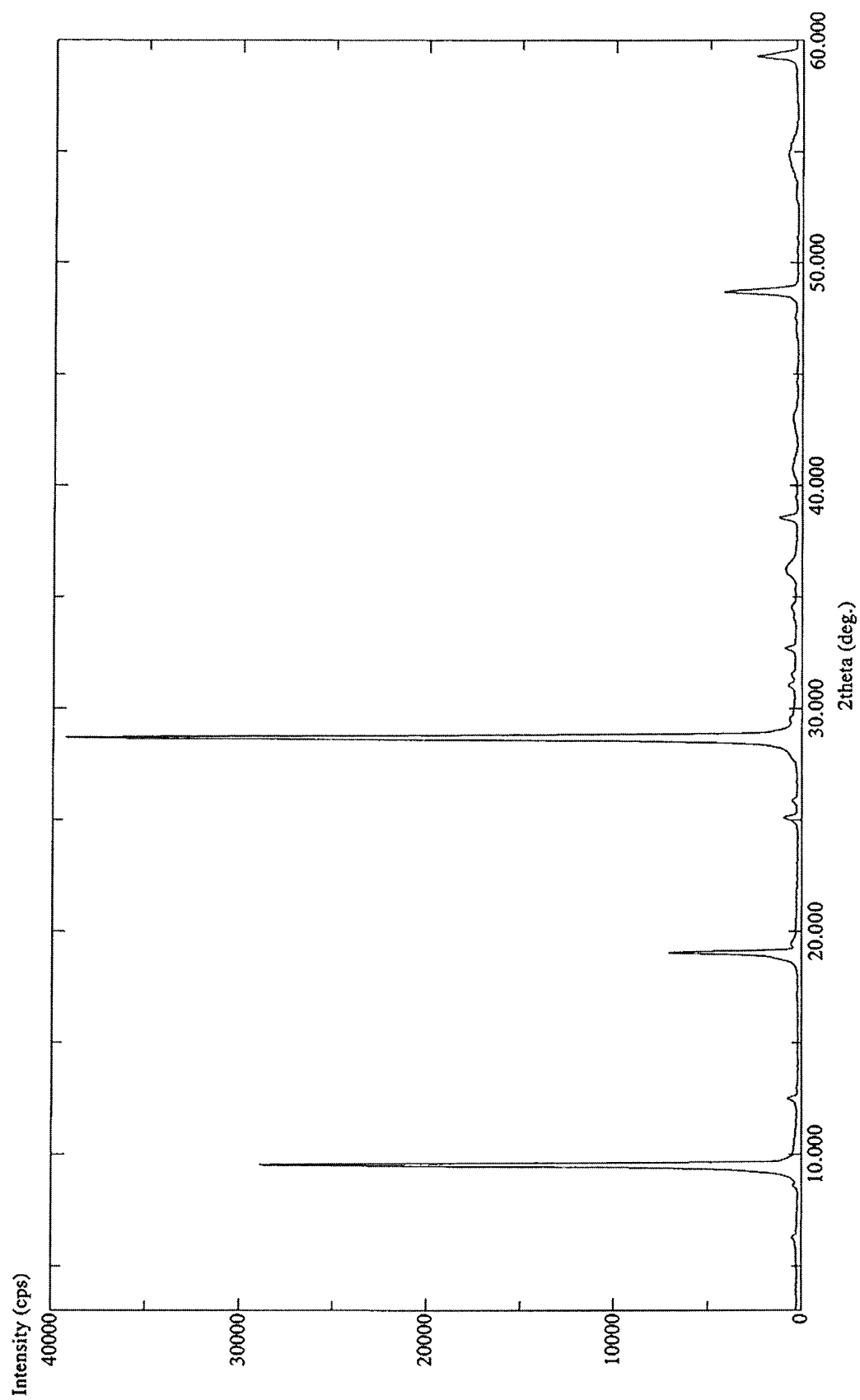
FIG. 13. Is a DRX of Talc
Figure 14:
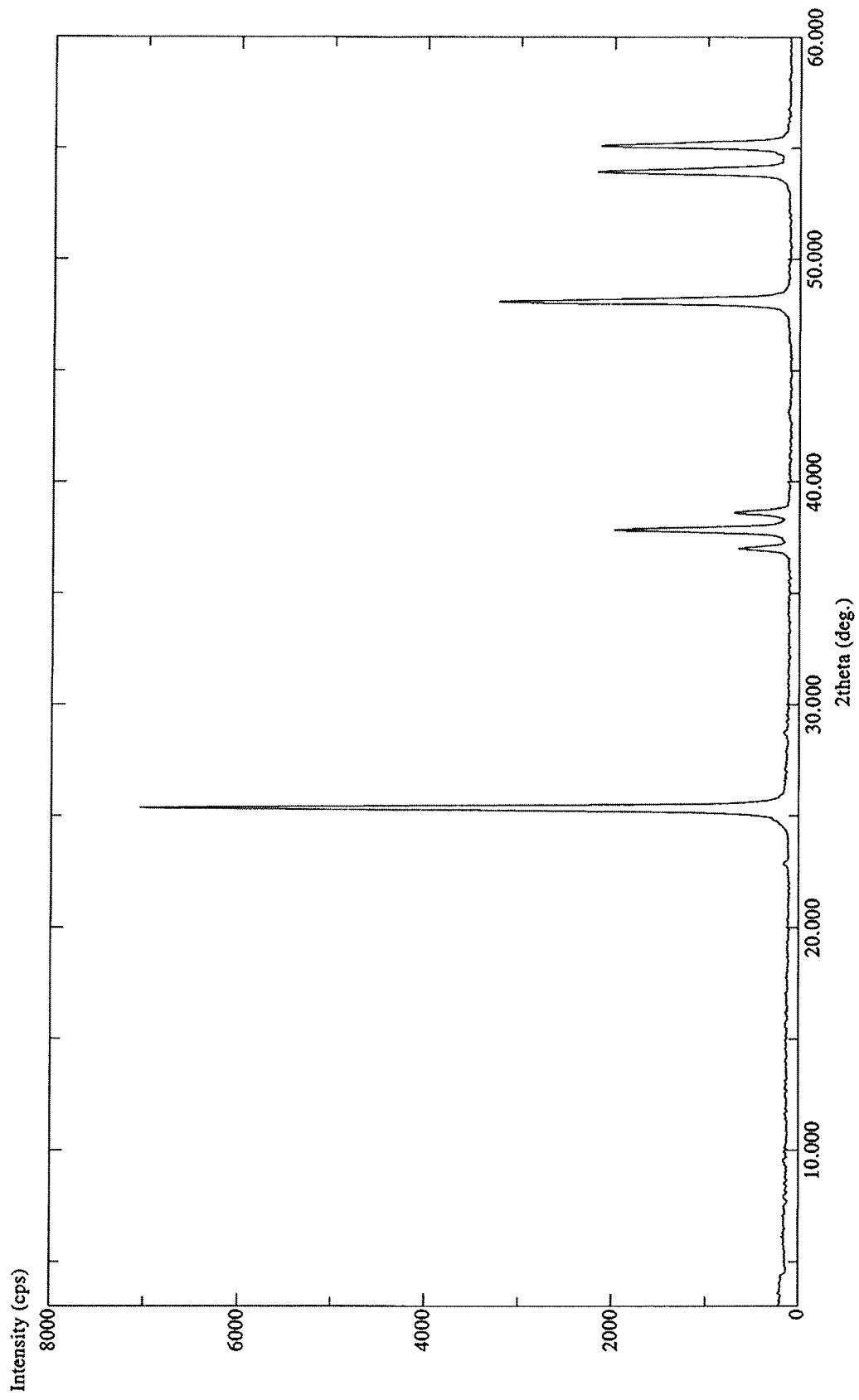
FIG. 14. Is a DRX of Titanium dioxide
Figure 15:
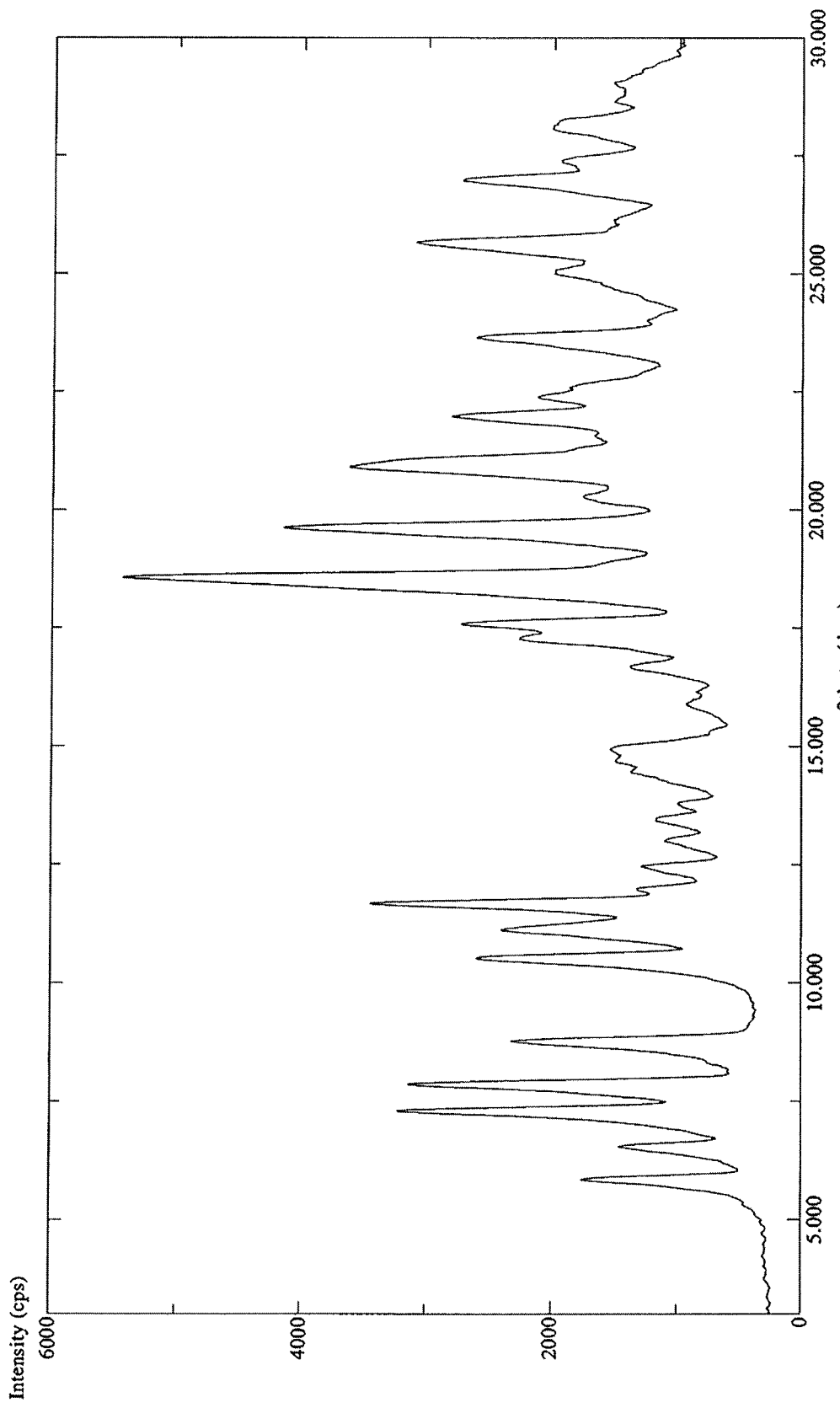
FIG. 15. Is a DRX of Rifaximin alpha form
Figure 16:
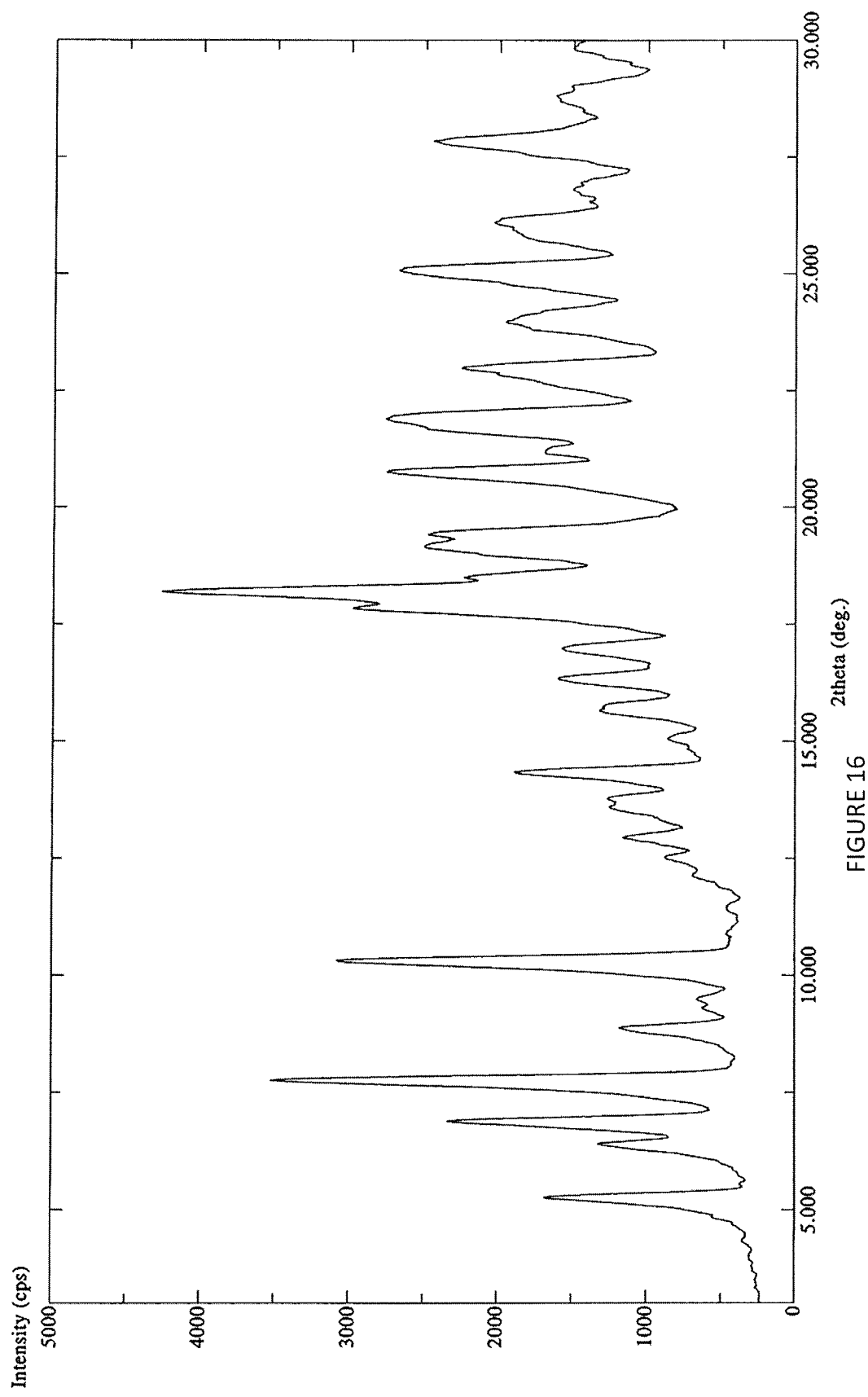
FIG. 16. Is a DRX of Rifaximin beta form

The uncoated tablets recovered from step c') according to the present invention is characterized by an X-Ray spectrum with characteristic 2theta values at (relative intensity): 5.28 (15%), 5.78 (23%), 6.52 (46%), 7.26 (47%), 7.88 (75%), 8.82 (42%), 10.52 (46%), 11.02 (45%), 11.58 (40%), 13.12 (37%), 14.48 (42%), 17.38 (56%), 17.72 (62%), 18.62 (93%), 19.54 (72%), 21.10 (87%), 21.64 (82%), 22.00 (100%). The following diagnostic peaks of the employed excipients are also detectable on the DRX spectrum (2theta values, in brackets the relative intensity of the diffraction peaks): 19.10 (50%) and 28.72 (40%) for talc; 22.36 (99%) microcrystalline cellulose; 21.10 (87%) for glycerol palmitostearate; 45.74 (36%) sodium starch glycolate; hydrate silicon dioxide is amorphous and does not present diffraction peaks (FIG. 5).

In an exemplary embodiment of the present invention, a film coated tablet comprising the above Rifaximin α/β polymorphic mixture, is prepared starting from a tableting mixture. The Rifaximin α/β polymorphic mixture is mixed with conventional excipients known in the art of film coated tablets, for example cellulose microcrystalline, sodium starch glycolate, glyceryl palmitostearate and talc. Other excipients can be used according to the general knowledge in this art. The components are mixed for a time sufficient to obtain a homogeneous mixture in a suitable mixing device. Typically, few minutes are sufficient. The so obtained blend is then compacted/granulated by using a conventional compactor (for example a WP50 N/75 compactor). The obtained granules are finished with a sieve, with a suitable dimension, such as for example about 20 mesh. Lubricants are added, for example one or more of glyceryl palmitostearate, talc, hydrated silicon dioxide. Conveniently also the excipients are previously sieved through a sieve of the same size of the granules. Mixing is carried out for a suitable time, typically few minutes, in a suitable mixer. The blend is compressed by means of a rotary tableting machine or any other conventional equipment.

In a preferred embodiment, the tablets according to the present invention have the following technological characteristics: Hardness—18.49±1.30 Kp; Thickness—5.48±0.06 mm; Friability—0.058%; Disintegration in purified water at 37° C.—1'20".

Film coating is carried out according to any suitable known technique, for example a coating pan by spraying a water suspension containing a film coating agent (such as polyvinyl alcohol, or other equivalent) and plasticizers (such as polyethylene glycol or other equivalent), and if desired an opacifier (for example titanium dioxide) and/or a coloring agent (for example red iron oxide). Preferably, the coated tablets are prepared keeping the tablet bed at a temperature below 40° C. for the entire coating process.

Packaging is done according conventional manufacturing practice, for example aluminum/plastic blister.

According to another object of the present invention, the polymorphic mixture of Rifaximin herein disclosed is for use as a medicament, in particular for the treatment of traveler's diarrhea and hepatic encephalopathy.

The dosage, way of administration and clinical indication can be decided by the expert of the art, based on the general knowledge, for example as shown in U.S. Pat. Nos. 7,902,206, 7,906,542, 8,158,644 and 7,928,115 for coated and uncoated tablets, hard and soft gelatin capsules and powders in sealed packets.

The following Examples further illustrate the invention.

Materials and Methods

X-Ray Diffraction spectra were registered by means of diffractometer (Rigaku-D-Max) from a start angle [½ 2-theta] of 5.000 to 60.000. The diffraction diagrams were obtained employing a Cu anode (Kα=1.54060 Å and Kα=1.54439 Å). The relative ratio between alpha and beta polymorphic forms were determined by DRX (powder) using a calibration curve obtained using two samples of Rifaximin prepared by mixing pure alpha (DRX: Enclosure 15) and pure beta (DRX: Enclosure 16) forms in a relative ratio of 80/20 and 90/10 (these samples were prepared according to EP1557421). The diagnostic diffraction peaks considered in order to quantify the relative ratio between the alpha and the beta form are the following:

Alpha form: diffraction peak at about 5.9 2theta
Beta form: diffraction peak at about 5.3 2theta The calibration curve was prepared taking into consideration the intensity of the diffraction peak at 5.2 2theta (beta form) divided for the intensity of the diffraction peak at 5.9 2theta (alpha form) (see FIG. 1).

Example 1

Preparation of Crude Wet Rifaximin

Rifamycin O (50 g) was dispersed in a mixture of demineralized water (60 ml) and ethyl alcohol (140 ml) under stirring at room temperature, then 2-amino-4-methylpyridine (20.8 g) was loaded. The reaction mixture is maintained under stirring at 20-30° C. for 20-23 hours.

After this period, L-ascorbic acid (1.4 g) was added to the reaction mixture and the pH corrected under stirring at room temperature to a final value of 6.0-6.5 by addition of 3M HCl water/ethanol 62/38 v/v solution. The reaction mixture was then cooled down at 8-12° C. maintained under stirring for 2 hours and filtered on a Büchner filter. The solid recovered on the filter (about 90.2 g of wet product with 54% of loss on drying; 30% of water content) was washed with a 1/1 ethanol/water mixture (242 ml) and utilized as such in the next step of crystallization. This new polymorphic form is defined by the DRX reported in FIG. 2. The characteristic 2theta values for this polymorphic form are (relative intensity): 4.88 (87%), 7.78 (74%), 12.76 (57%), 14.08 (59%), 14.66 (46%), 17.80 (50%), 18.34 (69%), 19.78 (80%), 21.22 (70%), 21.92 (74%), 23.18 (80%), 25.30 (100%).

Example 2

Preparation of Rifaximin α/β polymorphic mixture in a relative ratio of 87/13 from crude wet Rifaximin The wet crude Rifaximin recovered in the previous step was dispersed in ethanol (80.5 ml) and heated under stirring at 50-60° C. (a solution was obtained) then water was added (16.5 ml) maintaining the temperature at 50-60° C. The reaction mixture was cooled down to 28-33° C. to afford a precipitate. The obtained suspension was maintained at 28-33° C. under stirring for 2 hours, then cooled down at 20-25° C. and stirred at this temperature for 1 hour and finally to 0-5° C. and stirred at this temperature for 1 hour. The obtained suspension was filtered on a laboratory filter drier (GFD® Mod. PF00002ATEX) and the solid so recovered washed on the filter with water (62.2 ml).

The wet product recovered on the filter (defined by DRX powder and identified by us as purified wet Rifaximin; FIG.

Figure 17:
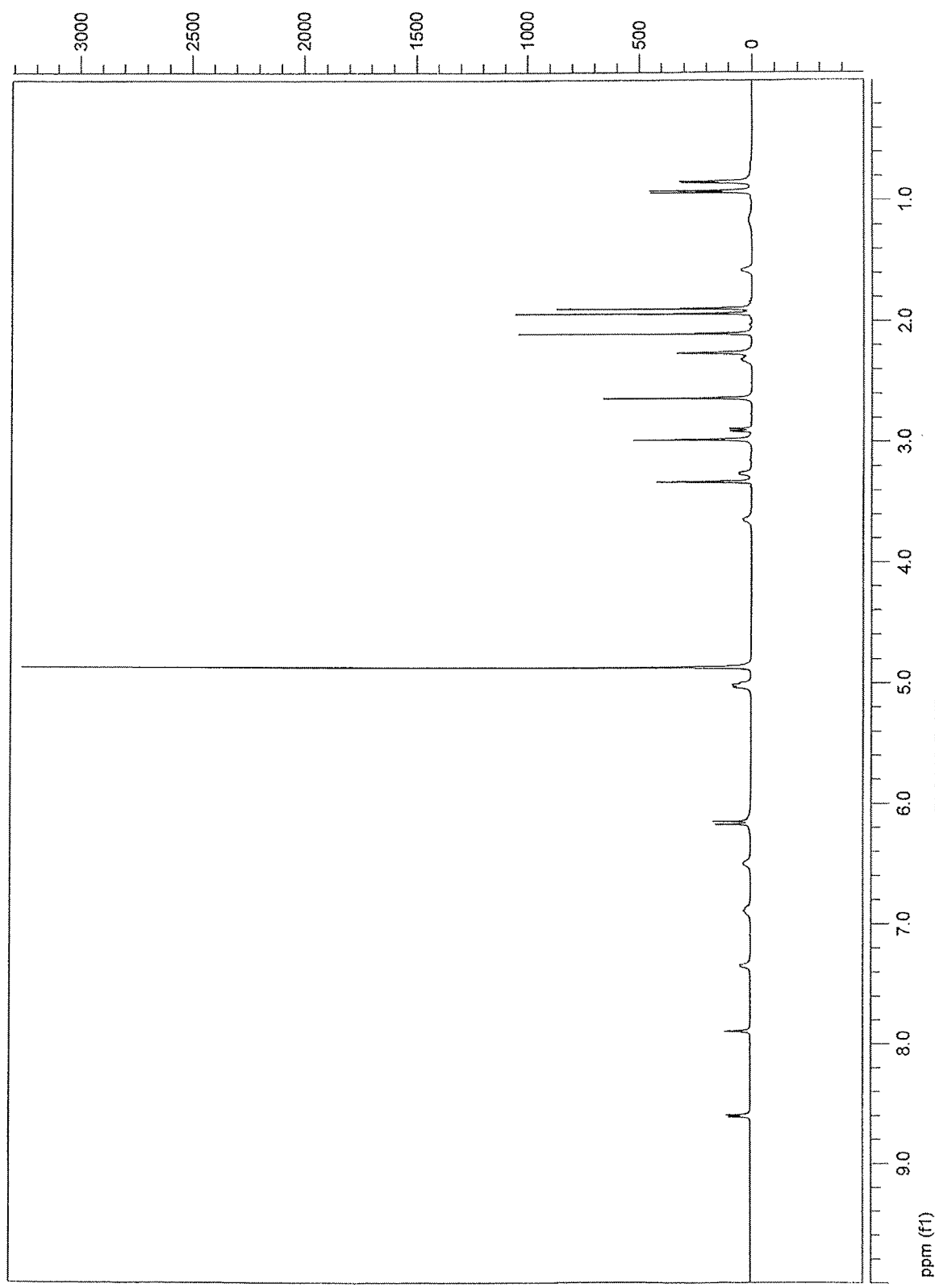
FIG. 17. Is a monodimensional $^1$H-NMR (500 MHz) spectrum of Rifaximin polymorphic mixture in tetradeuterated methanol.

3) was dried under stirring (15 rpm/m) at the temperature of 40° C. and under a nitrogen flow for 21 hours to reach a water content of 6.0% (determined by Karl Fisher). 32 g of Rifaximin as α/β polymorphic mixture with a relative ratio of 87/13 was obtained (determined by DRX powder as reported in the FIG. 4). The physico-chemical data of the obtained sample are in agreement with the proposed structure and with published literature data (R. Stradi et al. Journal Pharmaceutical and Biomedical Analysis, 51 (2010), 858-865); Enclosed the monodimensional $^1$H-NMR (500 MHz) spectrum of the obtained sample in tetradeuterated methanol (FIG. 17).

The relevant peaks of the DRX spectrum of the purified wet Rifaximin recovered on the filter are detectable at the following 2theta values (relative intensity): 5.78 (15%), 7.32 (27%), 8.16 (40%), 9.20 (44%), 10.74 (50%), 17.56 (42%), 18.04 (75%), 18.70 (100%), 20.02 (54%), 21.24 (73%), 22.32 (54%), 23.62 (46%), 25.66 (61%) (FIG. 3).

The relevant peaks of the DRX spectrum of Rifaximin α/β polymorphic mixture in a relative ratio of 87/13 are detectable at the following 2theta values (relative intensity): 5.32 (11%), 5.78 (19%), 6.50 (27%), 7.24 (45%), 7.82 (61%), 8.80 (100%), 10.50 (59%), 11.02 (35%), 11.58 (32%), 13.08 (20%), 14.42 (26%), 17.32 (48%), 17.68 (93%), 18.58 (79%), 19.52 (61%), 21.04 (52%), 21.60 (30%), 21.92 (46%) (FIG. 4).

Example 3

Consistency of the Polymorphic Mixture

The consistency of this procedure was checked repeating the process three times affording the same polymorphic mixture with a variability of ±3% (from 82/18 to 88/12 of α/β polymorphic mixture).

Example 4

Stability of the Polymorphic Mixture

The stability of a sample of Rifaximin α/β polymorphic mixture 88/12 using as primary packaging double polyethylene bags at room temperature was confirmed by repeating the DRX (powder) analysis of the same batch at time=0 and after 3 and 6 months Example 5

Dry Granulation and Tableting of Rifaximin α/β Polymorphic Mixture in a Relative Ratio of 85/15±3

Tableting Mixture Production

Rifaximin α/β polymorphic mixture in a relative ratio of 85/15±3 (452.86 g), Cellulose microcrystalline (259.90 g/Vivapur PH 102), Sodium starch glycolate (16.824 g), Glyceryl Palmitostearate (20.040 g/Precirol AT05) and Talc (1.203 g) are mixed for 5 minutes in a suitable mixing device. Blend is then compacted/granulated by using a compactor WP50 N/75.

Only a partial amount of these granules were utilized in the next step. The obtained granules (556.76 g) are finished with a 20 mesh sieve, added with Glyceryl Palmitostearate (14.87 g/Precirol AT05), Talc (4.68 g), Hydrated Silicon Dioxide (2.97 g/Syloid 244), being all the excipients previously sieved through a 20 mesh sieve, and mixed for 5 minutes in a suitable mixer. The composition of the tableting mixture is as follows:

Rifaximin Tablet Composition Dry Granules

|  | mg/tbs | % w/w |
| --- | --- | --- |
| Rifaximin | 550.0 | 54.1 |
| Cellulose microcrystalline Vivapur PH 102 | 340.0 | 33.4 |
| Sodium starch glycolate | 42.0 | 4.1 |
| Glyceryl Palmitostearate (Precirol ATO 5) | 50.0 | 4.9 |
| Hydrated Silicon Dioxide (Syloid 244) | 5.0 | 0.5 |
| Talc | 30 | 3 |
| Total | 1017 | 100 |

Tableting Results

Blend is compressed by means of a rotary tablet machine Ronchi EA8 equipped with 22×10 mm oval punches. Tablets with the following technological characteristics were obtained: Hardness—18.49±1.30 Kp; Thickness—5.48±0.06 mm; Friability—0.058%; Disintegration in purified water at 37° C.—1'20".

The formulation for the coated tablets is reported below: the film coating was carried out in a suitable coating pan by spraying a water suspension containing film coating agent (Polyvinyl alcohol) and plasticizers (Polyethylene Glycol) and opacifier (Titanium dioxide) and coloring agent (Red iron oxide). The coated tablets were prepared keeping the tablet bed at a temperature below 40° C. for the entire coating process.

Rifaximin tablet composition after coating process is below reported.

|  | mg/tbs | % w/w |
| --- | --- | --- |
| Rifaximin | 550.0 | 53.0 |
| Cellulose microcrystalline (Vivapur PH 102) | 340.0 | 32.8 |
| Sodium starch glycolate | 42.0 | 4.0 |
| Glyceryl Palmitostearate (Precirol ATO 5) | 50.0 | 4.82 |
| Hydrated Silicon Dioxide (Syloid 244) | 5.0 | 0.5 |
| Talc | 30 | 2.9 |
| Polyethylene Glycol 6000 | 1.6 | 0.15 |
| Polyvinyl alcohol | 15.0 | 1.4 |
| Red iron oxide | 0.4 | 0.04 |
| Titanium dioxide | 4.0 | 0.39 |
| Total | 1038 | 100 |

The obtained tablets before coating were mild grinded in a mortar and examined by DRX (powder): these analyses confirm that Rifaximin presents the unchanged relative ratio between the α/β polymorphic form of 85/15±3 (FIG. 5); on this DRX spectrum the following diagnostic peaks of the employed excipients are detectable: 19.10 (50%) and 28.72 (40%) for talc; 22.36 (99%) microcrystalline cellulose; 21.10 (87%) for glycerol palmitostearate; 45.74 (36%) sodium starch glycolate; hydrate silicon Dioxide is amorphous and does not present diffraction peaks.

In the enclosed FIGS. 6-14 are collected the DRX spectra of the employed excipients; the diffraction peaks of the excipients do not interfere with the diagnostics peaks utilized for the relative quantitation of Rifaximin α and β forms (see materials and methods).

What is claimed:

1. A Rifaximin polymorphic mixture of α/β form in a relative ratio of 85/15±3, characterized by an X-Ray spectrum with characteristic 2theta values at: 5.32, 5.78, 6.50, 7.24, 7.82, 8.80, 10.50, 11.02, 11.58, 13.08, 14.42, 17.32, 17.68, 18.58, 19.52, 21.04, 21.60, and 21.92.

2. A pharmaceutical composition comprising the polymorphic mixture of Rifaximin of claim 1, and a vehicle, excipient, or formulative ingredient.

3. The pharmaceutical composition of claim 2, wherein the pharmaceutical composition is a solid pharmaceutical composition.

4. The pharmaceutical composition of claim 3, wherein the pharmaceutical composition is a film coated tablet.

5. The pharmaceutical composition of claim 2, wherein the pharmaceutical composition comprises 550 mg of Rifaximin α/β polymorphic mixture of 85/15±3.

6. The pharmaceutical composition of claim 2, wherein the pharmaceutical composition further comprises excipients.

7. The pharmaceutical composition of claim 6, wherein the excipients comprise cellulose microcrystalline, sodium starch glycolate, glyceryl palmitostearate, hydrated silicon dioxide, and talc.

8. The pharmaceutical composition of claim 7, wherein the pharmaceutical composition further comprises polyvinyl alcohol, polyethylene glycol, titanium dioxide, and red iron oxide.

9. The pharmaceutical composition of claim 8, wherein the pharmaceutical composition has a hardness of 18.49±1.30 Kp, a thickness of about 5.48±0.06 mm, a friability of about 0.058%, and a disintegration in purified water at 37° C. of about 1'20".

10. A tablet, comprising the Rifaximin polymorphic mixture of claim 1 and a film coating.

11. A Rifaximin polymorphic mixture of α/β form in a relative ratio of 85/15±3, characterized by an X-Ray spectrum with characteristic 2θ values at 5.32, 5.78, 6.50, 7.24, 7.82, 8.80, 10.50, 11.02, 11.58, 13.08, 14.42, 17.32, 17.68, 18.58, 19.52, 21.04, 21.60, and 21.92, wherein said rifaximin polymorphic mixture is produced by drying wet Rifaximin at atmospheric pressure, at a temperature between 38 and 42° C. to reach a final water content of 6±2%.

* * * * *